US006946458B2

(12) United States Patent
Turos

(10) Patent No.: US 6,946,458 B2
(45) Date of Patent: *Sep. 20, 2005

(54) **N-THIOLATED BETA-LACTAMS: NOVEL ANTIBACTERIAL AGENTS FOR METHICILLIN-RESISTANT *STAPHYLOCOCCUS AUREUS***

(75) Inventor: Edward Turos, Temple Terrace, FL (US)

(73) Assignee: University of South Florida, Tampa, FL (US)

( * ) Notice: Subject to any disclaimer, the term of this patent is extended or adjusted under 35 U.S.C. 154(b) by 14 days.

This patent is subject to a terminal disclaimer.

(21) Appl. No.: 10/288,897

(22) Filed: Nov. 5, 2002

(65) Prior Publication Data

US 2003/0191108 A1 Oct. 9, 2003

Related U.S. Application Data

(63) Continuation-in-part of application No. 09/621,646, filed on Jul. 24, 2000, now Pat. No. 6,476,015.
(60) Provisional application No. 60/145,004, filed on Jul. 22, 1999, and provisional application No. 60/370,250, filed on Apr. 8, 2002.

(51) Int. Cl.$^7$ .................... C07D 205/08; A61K 31/397; A61P 31/04
(52) U.S. Cl. .................... 514/210.15; 540/355
(58) Field of Search .................... 540/355; 514/210.15

(56) References Cited

U.S. PATENT DOCUMENTS

| 4,938,949 A | 7/1990 | Borch et al. |
| 5,142,039 A | 8/1992 | Blaszczak et al. |
| 5,338,861 A | 8/1994 | Botta et al. |
| 6,476,015 B1 * | 11/2002 | Turos et al. ........... 514/210.15 |

OTHER PUBLICATIONS

Hawley, G. "The Condensed Chemical Dictionary", 1977, Van Nostrand, New York, p. 498.*
Roberts, J.D. and M.C. Caserio "Basic Principles of Organic Chemistry", Benjamin, New York, 1964, p. 529.*
Burnett, D.A. et al. "β–Lactams from Esters and Sulfenimines: A New Route to Monobactams" *J. Org. Chem.,* 1986, 51(10):1929–1930.*
Shah, N.V. and L.D. Cama "Synthesis of a Novel Carbapenem–Potassium (5R,6R)–1, 1–Difluro–2–Phenyl–6–(1R–Hydroxyethel)–Carbapen–2EM–3–Carboxylate. The Use of New N–Protecting Group in β–Lactam Synthesis" *Heterocycles,* 25:221–227.*
An and Dou, "Cleavage of Retinoblastoma Protein during Apoptosis: An Interleukin 1β–converting Enzyme–like Protease as Candidate," *Cancer Research,* 1996, vol. No. 56, pp. 438–442.

An, et al., "Novel dipeptidyl proteasome inhibitors overcome Bcl–2 protective function and selectivity accumulate the cyclin–dependent kinase inhibitor p27 and induce apoptosis in transformed, but not normal, human fibroblasts," *Cell Death and Differentiation,* 1998, vol. No. 5, pp. 1062–1075.
Desoize, "Anticancer Drug Resistance and Inhbition of Apoptosis," *Anticancer Research,* 1994, vol. No. 14, pp. 2291–2294.
Dou, "Putative roles of retinoblastoma protein in apoptosis," *Apoptosis,* 1997, vol. No. 2, pp. 5–18.
Drexler, et al., "Continuous hematopoietic cell lines as model systems for leukemia—lymphoma research," *Leukemia Research,* 2000, vol. No. 24, pp. 881–911.
Earnshaw, "Nuclear changes in apoptosis," *Current Opinion in Cell Biology,* 1995, vol. No. 7, pp. 337–343.
Fattman, et al. "Sequential two–step cleavage of the retinoblastoma protein by caspase–3/–7 during etoposide–induced apoptosis," *Oncogene,* 2001, vol. No. 20, pp. 2918–2926.
Fisher, "Apoptosis in Cancer Therapy: Crossing the Threshold," *Cell,* 1994, vol. No. 78, pp. 539–542.
Gao and Dou, "N–Terminal Cleavage of Bax by Calpain Generates a Potent Proapoptotic 18–kDa Fragment that Promotes Bcl–2–Independent Cytochrome C Release and Apoptotic Cell Death," *Journal of Cellular Biochemistry,* 2000, vol. No. 80, pp. 53–72.
Green and Reed, "Mitochondria and Apoptosis," *Science,* 1998, vol. No. 281, pp. 1309–1312.
Harrison, "Molecular Mechanisms of Drug Resistance in Tumours," *Journal of Pathology,* 1995, vol. No. 175, pp. 7–12.
Jänicke, et al., "Specific cleavage of the retinoblastoma protein by an ICE–like protease in apoptosis," *The EMBO Journal,* 1996, vol. No. 15, Issue No. 24, pp. 6969–6978.
Kellen, "Molecular Interrelationships in Multidrug Resistance (Review)," *Anticancer Research,* 1994, vol. No. 14, pp. 443–436.
Kummer, et al., "Apoptosis induced by Withdrawal of Trophic Factors is Mediated by p38 Mitogen–activated Protein Kinase," *The Journal of Biological Chemistry,* 1997, vol. No. 272, Issue No. 33, pp. 20490–20494.
Lazebnik, et al. "Cleavage of poly(ADP–ribose) polymerase by a proteinase with properties like ICE," *Nature,* 1994, vol. No. 371, pp. 346–347.
Lee, et al., "Apoptosis and signal transduction: clues to a molecular mechanism," *Current Opinion in Cell Biology* 1993, vol. No. 5, pp. 286–291.

(Continued)

*Primary Examiner*—Venkataraman Balasubramanian
(74) *Attorney, Agent, or Firm*—Saliwanchik, Lloyd & Saliwanchik

(57) ABSTRACT

The invention relates generally to novel N-thiolated β-lactams. More specially, the invention relates to the use of these novel antibacterial agents in the treatment or inhibition of methicillin-resistant *Staphylococcus aureus*.

14 Claims, 10 Drawing Sheets

OTHER PUBLICATIONS

Li, et al., "Cleavage of BID by Caspase 8 Mediates the Mitochondrial Damage in the Fas Pathway of Apoptosis," *Cell,* 1998, vol. No. 94, pp. 491–501.

Martin and Green, "Protease Activation during Apoptosis: Death by a Thousand Cuts?" *Cell,* vol. No. 82, pp. 349–352.

Menter, et al., "Selenium Effects on Prostate Cell Growth," *Cancer Epidemiology, Biomarkers & Prevention,* 2000, vol. No. 9, pp. 1171–1182.

Nam, et al., "Ester Bond–containing Tea Polyphenols Potently Inhibit Proteasome Activity in Vitro and in Vivo," *The Journal of Biological Chemistry,* 2001, vol. No. 276, pp. 13322–13330.

Pfundt, et al., "In situ demonstration of phosphorylated c–jun and p38 MAP kinase in epidermal keratinocytes following ultraviolet B irradiation of human skin," *Journal of Pathology,* 2001, vol. No. 193, pp. 248–255.

Raingeaud, et al., "Pro–inflammatory Cytokines and Environmental Stress Cause p38 Mitogen–activated Protein Kinase Activation by Dual Phosphorylation on Tyrosine and Threonine," *The Journal of Biological Chemistry,* 1995, vol. No. 270, Issue No. 13, pp. 7420–7426.

Sanchez–Prieto, et al., "A Role for the p38 Mitogen–activated Protein Kinase Pathway in the Transcriptional Activation of p53 on Genotoxic Stress by Chemotherapeutic Agents," *Cancer Research,* vol. No. 60, pp. 2464–2472.

Smith and Dou, "Green tea polyphenol epigallocatechin inhibits DNA replication and consequently induces leukemia cell apoptosis," *International Journal of Molecular Medicine,* 2001, vol. No. 7, pp. 645–652.

Smith, et al., "Regulation of tumor cell apoptotic sensitivity during the cell cycle (Review)," *International Journal of Molecular Medicine,* 2000, vol. No. 6, pp. 1–5.

Smith, et al., "A Novel β–Lactam Antibiotic Activates Tumor Cell Apoptotic Program by Inducing DNA Damage," *Molecular Pharmacology,* 2002, vol. No. 61, pp. 1348–1358.

Staudinger, H., "Diphenylketen," Mittheilungen aus dem chemischen Institut der Universität Strassbur zur *Kenntniss der Ketene,* 1908 (1st edition), pp. 51–123.

Thornberry and Lazebnik, "Caspases: Enemies Within," *Science,* 1998, vol. No. 281, pp. 1312–1316.

Turos, et al., "N–Thiolated Bicyclic and Monocyclic β–Lactams," *Tetrahedron,* 2000, vol. No. 56, pp. 5571–5578.

Watabe, et al., "MT–21 is a Synthetic Apoptosis Inducer that Directly Induces Cytochrome c Release from Mitochondria," *Cancer Research,* 2000, vol. No. 60, pp. 5214–5222.

Wu and Wu, "Receptor–mediated in Vitro Gene Transformation by a Soluble DNA Carrier System," *The Journal of Biological Chemistry,* 1987, vol. No. 262, pp. 4429–4432.

Binder, S. et al. "Emerging Infectious Diseases: Public Health Issues for the 21st Century" *Science,* May 21, 1999, 284:1311–1313.

Boyd, D.B. et al. "Heteroatom–Activated β–Lactam Antibiotics: Considerations of Differences in the Biological Activity of [[3(S)–(Acylamino)–2–oxo–1–azetidinyl]oxy] acetic Acids (Oxamazins) and the Corresponding Sulfur Analogues (Thiamazins)" *J. Med. Chem.,* 1987, 30:528–536.

Breuer, H. et al., "[(2–oxo–1–azetidinyl)oxy]acetic Acids: A New Class of Synthetic Monobactams" *J. Antibiotics,* Jun. 1985, 38(6):813–818.

Champney, W.S. and C.L. Tober "Evernimicin (SCH27899) Inhibits both Translation and 50S Ribosomal Subunit Formation in *Staphylococcus aureus* Cells" *Antimicrob. Agents and Chemotherapy,* Jun. 2000, 44(6):1413–1417.

Lim, D.V. et al. "Radiolabeling of and Macromolecular Syntheses in *Neisseria gonorrhoeae* Types 1 and 4" *Applied and Envion. Microbiology,* Feb. 1977, 33(2):328–333.

Long, T.E. and E. Turos "N–Thiolated β–Lactams" *Curr. Med. Chem.–Anti–Infective Agents,* 2002, 1(3):251–268.

Ren, X. et al., "Synthesis of Inversely–Fused Bicyclic β–Lactams" *J. Org. Chem.,* 1995, 60(16):4980–4981.

Ren, X. et al. "Studies on Nonconventionally Fused Bicyclic β–Lactams" *J. Org. Chem.,* 1998, 63(24):8898–8917.

Slusarchyk, W.A. et al. "Monobactams; Ring Activating N–1–Substituents in Monocyclic β–Lactam Antibiotics" *Heterocycles,* 1984, 21(1):191–209.

Sykes, R.B. et al. "Monocyclic β–lactam antibiotics produced by bacteria" *Nature,* Jun. 11, 1981, 291:489–491.

Turos, E. et al. "N–Thiolated Bicyclic and Monocyclic β–Lactams" *Tetrahedron,* 2000, 56:5571–5578.

Turos, E. et al. "N–Thiolated β–Lactams: Novel Antibacterial Agents for Methicillin–Resistant *Staphylococcus aureus*" *Bioorganic & Med. Chem. Letters,* 2002, 12:2229–2231.

Woulfe, S.R. and M.J. Miller "The Synthesis of Substituted [[3(S)–(Acylamino)–2–oxy–1–azetidinyl]thio]acetic Acids" *J. Org. Chem.,* 1986, 51:3133–3139.

* cited by examiner

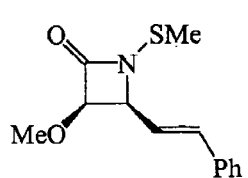 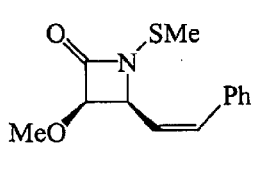 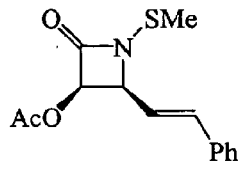 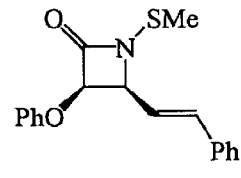
FIG. 3A  FIG. 3B  FIG. 3C  FIG. 3D
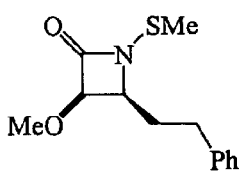 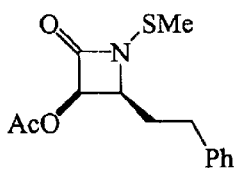 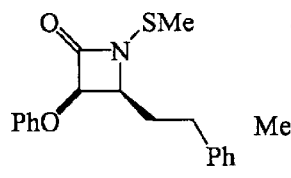 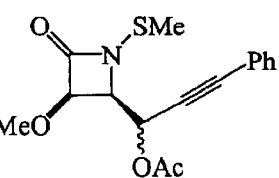
FIG. 3E  FIG. 3F  FIG. 3G  FIG. 3H
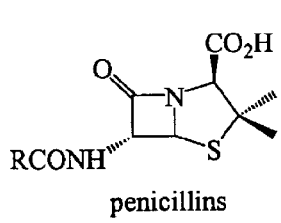 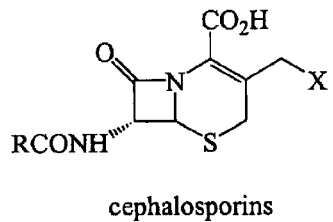 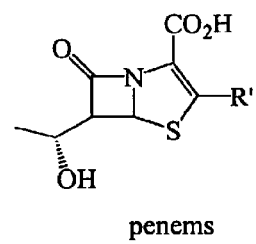
penicillins  cephalosporins  penems
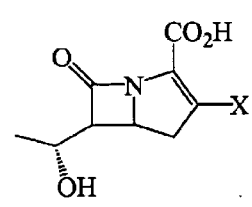 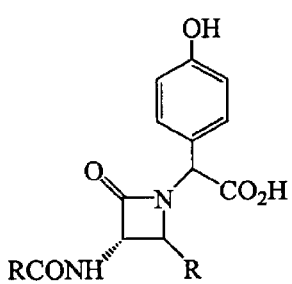 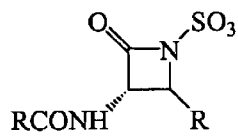
carbapenems  nocardicins  monobactams
FIG. 4

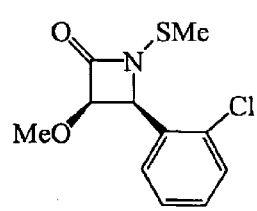 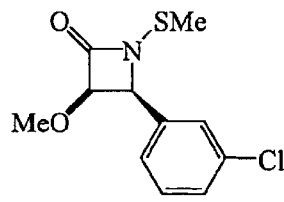 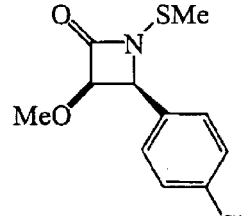 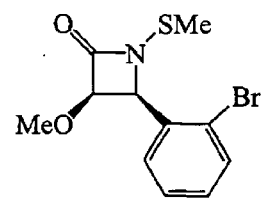
FIG. 7A     FIG. 7B     FIG. 7C     FIG. 7D
 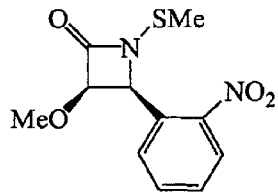 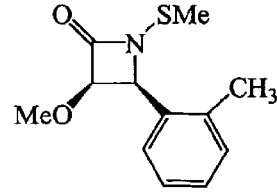
FIG. 7E     FIG. 7F     FIG. 7G
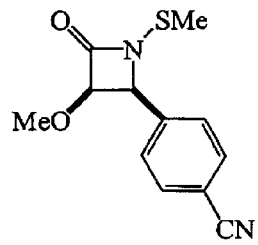 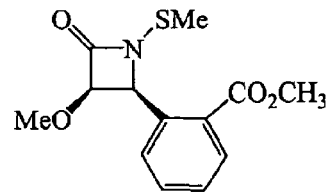 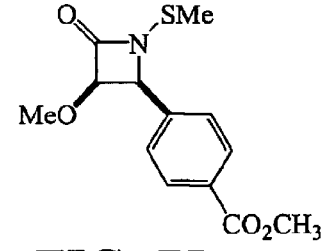
FIG. 7H     FIG. 7I     FIG. 7J

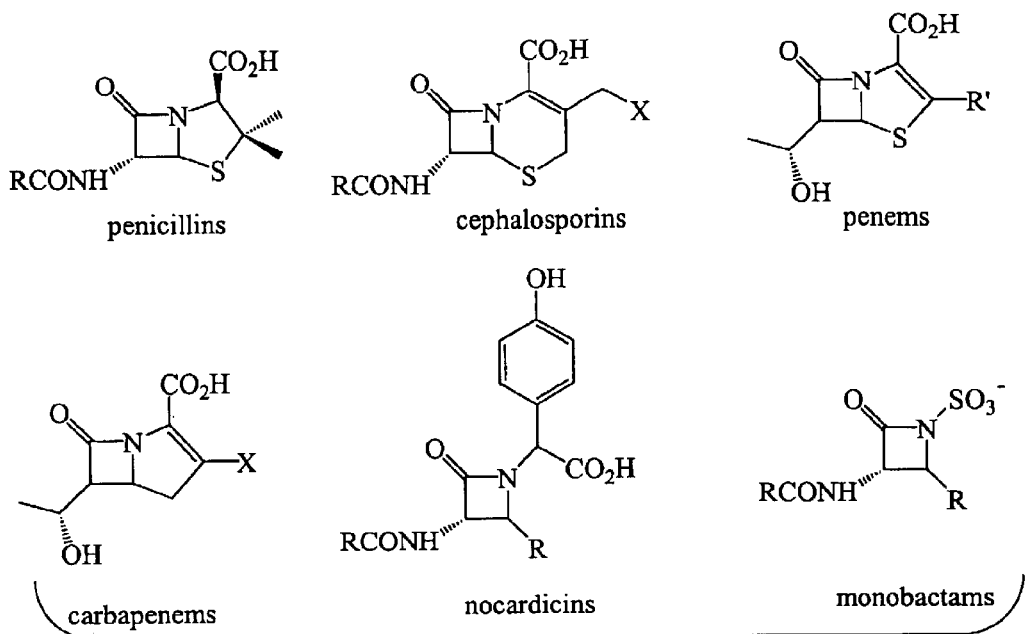
FIG. 10
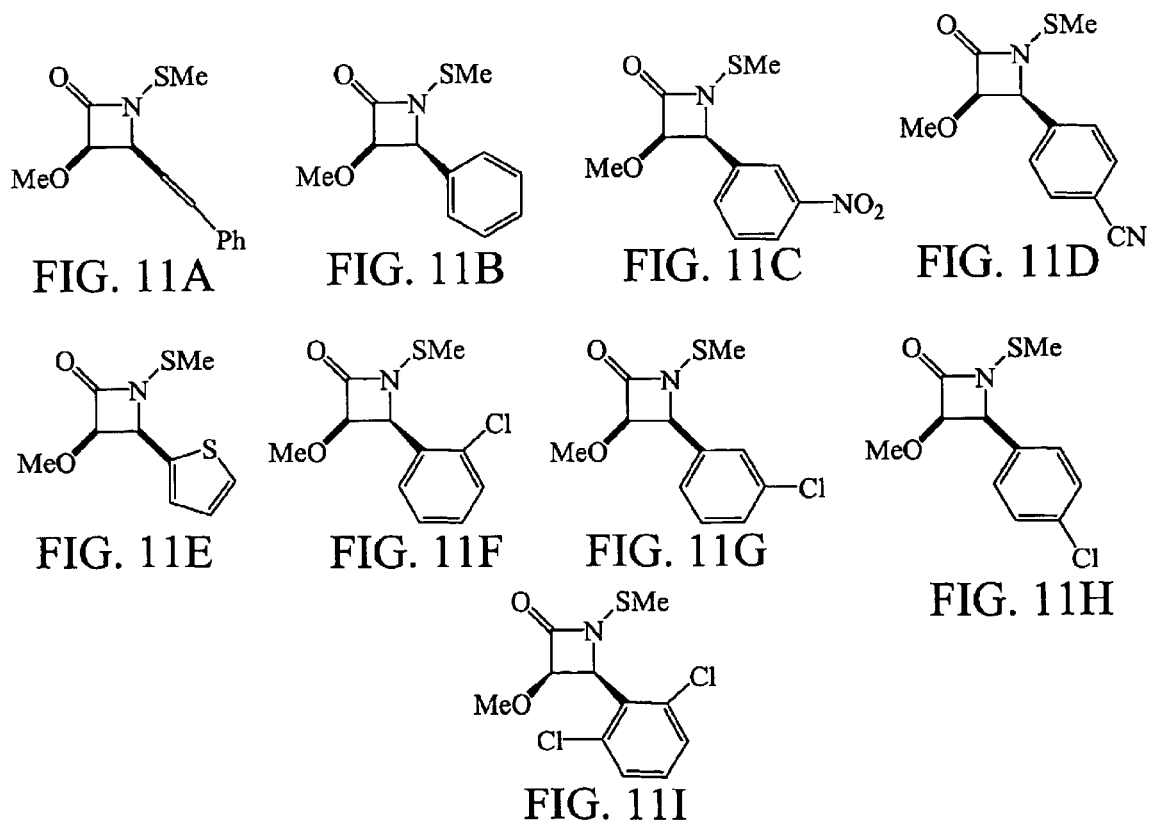
FIG. 11A  FIG. 11B  FIG. 11C  FIG. 11D
FIG. 11E  FIG. 11F  FIG. 11G  FIG. 11H
FIG. 11I

N-THIOLATED BETA-LACTAMS: NOVEL ANTIBACTERIAL AGENTS FOR METHICILLIN-RESISTANT *STAPHYLOCOCCUS AUREUS*

CROSS-REFERENCE TO RELATED APPLICATIONS

The present application is a continuation-in-part of U.S. application Ser. No. 09/621,646, filed Jul. 24, 2000 now U.S. Pat. No. 6,476,015, which claims the benefit of U.S. Provisional Application Ser. No. 60/145,004, filed Jul. 22, 1999; and claims the benefit of U.S. Provisional Application Ser. No. 60/370,250, filed Apr. 8, 2002, which are hereby incorporated by reference herein in their entirety, including any figures, tables, nucleic acid sequences, amino acid sequences, or drawings.

BACKGROUND OF INVENTION

The clinical use of antibiotics in the $20^{th}$ century has substantially decreased morbidity from bacterial infections. The early success of penicillin was extended by various sulfonamide drugs developed in the 1930s, and subsequently by a "golden" period of discovery, between 1945 and 1970, during which a wide array of highly effective agents are discovered and developed (Chopra, I., et al., "The Search for Antimicrobial Agents Effective against Bacteria Resistant to Multiple Antibiotics" *Antimicrobial Agents and Chemotherapy*, 1997, 41:497–503).

However, since the 1980s the introduction of new antibiotics has slowed, and, concurrently, there has been an alarming increase in bacterial resistance to existing agents that now constitutes a serious threat to public health (Brown, A. G. "Discovery and Development of New β-Lactam Antibiotics" *Pure & Appl. Chem.*, 1987, 59:475–484). Hospitals, nursing homes and infant day care centers have become breeding grounds for the most tenacious drug-resistant pathogens ("Frontiers in Biotechnology" *Science*, 1994, 264:359–393). There has been an alarming rise in drug resistant *staphylococci, enterococci, streptococci*, and *pneumococci* infections, and a rise in tuberculosis, influenza and sepsis.

For several decades, β-lactam antibiotics have been widely used to control bacterial infections. Since the discovery of penicillin, countless numbers of analogues have been prepared and tested (see for example: U.S. Pat. No. 5,142,039 (Blaszczak et al.) and U.S. Pat. No. 5,338,861 (Botts et al.)), and a variety of successful modifications have been made to the five-membered ring, including (1) replacement of the sulfur atom with carbon or oxygen, (2) oxidation of the sulfur to the sulfoxide or sulfone, (3) enlargement to a larger ring, (4) incorporation of unsaturation, (5) attachment of additional fused rings, and (6) removal of the five-membered ring. As a result, new β-lactam ring systems have been introduced, including the penems, cephalosporins, carbapenems, oxapenems, oxacephams, as well as monocyclic, spirocyclic, and multicyclic β-lactams. In the case of monocyclic β-lactams (Sykes, R. B. et al. "Monocyclic β-Lactam Antibiotics Produced by Bacteria" *Nature*, 1981, 291:489–490), which directly relates to the present invention, removal of the five-membered ring leaves a four-membered β-lactam ring, the structural core of which is 2-azetidinone (1):

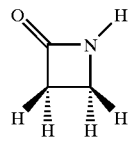

(1)

Monocyclic antibiotics successfully developed by derivatization of this core structure include the monobactams (Slusarchyk, W. A. et al. "Monobactams: Ring Activating N-1-Substituents in Monocyclic β-Lactam Antibiotics" *Heterocycles*, 1984, 21:191–209), which have 2-oxoazetidine sulfonic acid as their characteristic structure. A key feature of the monobactams is the activation of the β-lactam ring towards nucleophilic attack by bacterial transpeptidases that is caused by the electron-withdrawing potential of the sulfonated nitrogen atom. Alternative activating groups for monobactam derivatives have been discovered, including phosphate, phosphonate, and analogues in which a spacer atom is interposed between the ring nitrogen and activating group (Breuer, H. et al. "[(2-oxo-1-azetidinyl)oxy]acetic acids: a new class of synthetic monobactams" *J. Antibiotics*, 1985, 38:813–818; Slusarchyk, W. A. et al. "Monobactams: Ring Activating N-1-Substituents in Monocyclic β-Lactam Antibiotics" *Heterocycles*, 1984, 21:191–209).

The primary targets of β-lactams are the penicillin binding proteins, a group of bacterial proteins that mediate the final step of bacterial cell wall biosynthesis in which a terminal alanine-alanine linkage of a peptidoglycan strand is cleaved by an active site serine and cross-linked to another peptidoglycan fragment, thus strengthening the bacterial cell wall. Penicillin interrupts this cross-linking step by acylating the serine with its reactive β-lactam ring. Following acylation, ring opening results in further chemical fragmentations that are deleterious to the enzyme. Also among the penicillin binding proteins are the β-lactamases; enzymes that degrade β-lactams. Clavulinic acid targets these enzymes, and is therefore useful in conjunction with established penicillins in combination therapies for combating certain resistant strains of bacteria (Chopra, I. et al. "The Search for Antimicrobial Agents Effective against Bacteria Resistant to Multiple Antibiotics" *Antimicrobial Agents and Chemotherapy*, 1997, 41:497–503).

Infections caused by methicillin-resistant *Staphylococcus aureus* (MRSA) are becoming extremely difficult to treat with conventional antibiotics, leading to a sharp rise in clinical complications (Binder, S. et al. *Science*, 1999, 284:1311). For additional articles and discussions on antimicrobial drug resistance: http://www.cdc.gov/ncidod/dbmd/antibioticresistance. The need for new antibiotics and protocols for treating MRSA infections is extremely serious.

There is a clear need for new antibacterial agents to combat pathogenic bacteria that have become resistant to current antibiotics. Towards this end, a novel class of derivatized, N-thiolated, monocyclic β-lactams have been developed in the present invention, that exhibit strong antibacterial activity against a wide variety of species and strains, including methicillin-resistant *Staphylococcus aureus*.

BRIEF SUMMARY OF THE INVENTION

A novel family of lipophilic β-lactam antibacterials and antibiotics are described herein that are effective against MRSA, and whose mode of action and structure-activity profiles differ dramatically from those of traditional β-lactam drugs (*Chemistry and Biology of β-Lactam Antibiotics*, Morin, R. B. and M. Gorman, Eds; Academic: New York, 1982, Vols. 1–3). Of particular importance, is the selectivity for *Staphylococcus* bacteria over most other common microorganisms, and the stability to β-lactamase proteins, represented by the β-lactam molecules described herein.

The general structure of these N-1 thiolated monolactam is:

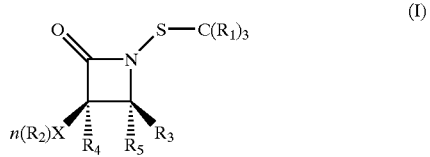

(I)

wherein $R_{1-5}$ are independently hydrogen, alkyl, heteroalkyl, aryl, heteroaryl, alkenyl, or alkynyl; X is H, C or O; and n=0 to 3.

It is an object of the present invention to provide these compounds, including their salts, hydrates, and in combinations with suitable pharmaceutical carriers, as antibacterial and antibiotic agents.

It is a further object of this invention to provide such compounds, wherein $R_4$ and $R_5$ are hydrogen, and $—C(R_1)_3$ is aryl or heteroaryl.

It is a further object of this invention to provide antibacterial and antibiotic agents with varying bacterial strain specificities and efficacies, by the expedient means of varying substituents of the 2-azetidinone ring, including but not limited to nitrogen (N-1) methylthio or benzylthio moieties, and substitutions at the $C_3$ and $C_4$ positions.

It is a further object of this invention to provide methods for inhibiting the growth of bacteria by administering the compounds of the present invention, and to provide methods for the treatment of bacterial infections of a patient, in which one or more doses of an effective amount of the compounds and compositions of the present invention are administered to a patient.

It is a further object of this invention to provide compounds and compositions suitable for the treatment of gonorrhea.

It is a further object of this invention to provide a method of inhibiting methicillin-resistant *Staphylococcus aureus* infection.

It is a further object of this invention to provide a mechanism of inhibiting infection comprising administering an N-thiolated β-lactam antibacterial compound to a patient in need thereof, where said antibacterial compound affects events within the cytoplasm of the cell.

It is a further object of this invention to provide a mechanism of inhibiting bacterial infection by a means other than inhibiting cell wall cross-linking.

It is a further object of this invention to provide a mechanism of inhibiting bacterial infection through the use of an antibacterial compound that does not block bacterial cell growth by inhibiting penicillin binding proteins.

The present invention confers numerous advantages over the compounds of the prior art, including the following: ease of synthesis, whereby compounds with diverse substituents may be synthesized and tested for antibacterial and antibiotic activity; the invention provides novel antibacterial and antibiotic agents to which bacterial pathogens have not yet acquired resistance; and the invention provides novel compounds for the treatment of increasingly common and resistant diseases such as gonorrhea. Surprisingly, the inventors have found that antibacterial and antibiotic activities can be obtained in compounds that do not possess traditional activating groups attached to the nitrogen, as required for activity in conventional monobactams which contain, for example, a sulfonic acid group. The inventors have also surprisingly discovered that derivatization of structure (I) at the positions indicated by the $R_{1-5}$ and X, results in compounds exhibiting different specificities for different bacterial pathogens, in a manner that is currently not possible to predict a priori. This aspect is therefore an unobvious benefit of the present invention. The present invention fulfills an urgent need in that novel compounds are urgently required as bacterial pathogens increasingly acquire immunity towards the present arsenal of antibiotics.

BRIEF DESCRIPTION OF DRAWINGS

FIGS. 2B–2D show the cyclization of the monocyclic lactam of FIG. 2B to the bicyclic lactam of FIG. 2D.

FIGS. 3A–3H show a series of structurally related $C_4$-substituted lactams.

FIG. 4 shows common β-Lactam Antibiotics.

FIGS. 7A–7J show halogenated compounds.

FIG. 10 shows traditional β-lactam drugs.

FIGS. 11A–11I show a series of other $C_4$-substituted derivatives.

FIG. 14A shows untreated MRSA cells. FIG. 14B shows MRSA treated with 6. FIG. 14C shows MRSA treated with penicillin G.

DETAILED DISCLOSURE OF THE INVENTION

Figure 1A:
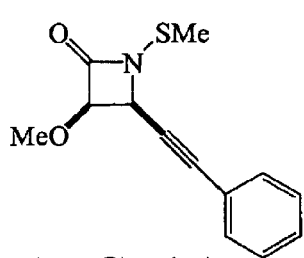
FIGS. 1A–1I show N-Methylthio β-lactam antibacterials.
Figure 1B:
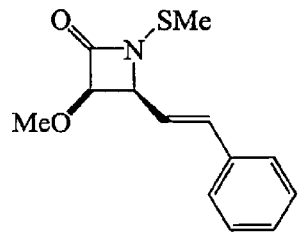
Figure 1C:
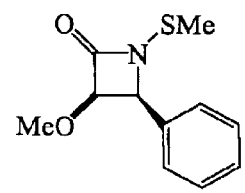

The term "N-1 thiolated monobactam" is used herein to refer to a monocyclic 4-membered beta-lactam compound comprising a 4-azetidinone ring in which the ring nitrogen (N-1) atom is covalently bonded to a sulfur that is covalently bonded to a carbon-centered moiety, and which may be further modified as described herein. Specifically, referring now to compound (I), X may be a hydrogen (in which case, n is preferably zero), or a carbon atom (in which case, n is preferably 3), or an oxygen atom (in which case, n is preferably 1), and $R_2$ may be any substituent as herein defined. Similarly, $R_1$ and $R_{3-5}$ may be independently any substituent as herein defined.

Thus, in preferred embodiments, $R_1$ is hydrogen or benzyl, and in most preferred embodiments $R_1$ is hydrogen. Substituents comprising —$X(R_2)_n$ are preferably methoxy and hydrogen, and most preferably methoxy. $R_3$ may be alkyl, heteroalkyl, aryl, heteroaryl, alkenyl, or alkynyl. Preferred $R_3$ substituents are phenylethynyl, acetoxy, 1-propenyl, ortho-chlorophenyl, ortho-nitrophenyl, 2-thiophene, or S,S-dioxo-thiophene. $R_4$ and $R_5$ may be independently alkyl, heteroalkyl, aryl, heteroaryl, alkenyl, or alkynyl groups. In preferred embodiments, $R_4$ and $R_5$ are H.

The following definitions are used, unless otherwise described. Halo is fluoro, chloro, bromo, or iodo. "Alkyl," "alkoxy," etc. denote both straight and branched groups; but reference to an individual radical such as "propyl" embraces only the straight chain radical, a branched chain isomer such as "isopropyl" being specifically referred to. "Aryl" denotes a phenyl radical or an ortho-fused bicyclic carbocyclic radical having about nine to ten ring atoms in which at least one ring is aromatic. "Heteroaryl" encompasses a radical attached via a ring carbon of a monocyclic aromatic ring containing five or six ring atoms consisting of carbon and one to four heteroatoms each selected from the group consisting of non-peroxide oxygen, sulfur, and $N(R_x)$ wherein $R_x$ is absent or is hydrogen, oxo, alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto. "Heteroalkyl" encompasses the replacement of a carbon atom within an alkyl chain with a heteroatom; e.g., replacement with an element other than carbon such as N, S, or O, including both an alkyl interrupted by a heteroatom as well as an alkyl substituted by a heteroatom.

It will be appreciated by those skilled in the art that compounds of the invention having one or more chiral center(s) may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis, from optically-active starting materials, by chiral synthesis, or by chromatographic separation using a chiral stationary phase), and how to determine antibacterial activity using the tests described herein, or using other tests which are well known in the art.

Specific and preferred values listed below for radicals, substituents, and ranges, are for illustration only; they do not exclude other defined values or other values within defined ranges for the radicals and substituents.

Specifically, "alkyl" can include methyl, ethyl, propyl, isopropyl, butyl, iso-butyl, sec-butyl, pentyl, 3-pentyl, hexyl, heptyl, octyl, nonyl, decyl, undecyl, dodecyl, tridecyl, tetradecyl or pentadecyl; "alkenyl" can include vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl, 1-heptenyl, 2-heptenyl, 3-heptenyl, 4-heptenyl, 5-heptenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl, 9-decenyl; 1-undecenyl, 2-undecenyl, 3-undecenyl, 4-undecenyl, 5-undecenyl, 6-undecenyl, 7-undecenyl, 8-undecenyl, 9-undecenyl, 10-undecenyl, 1-dodecenyl, 2-dodecenyl, 3-dodecenyl, 4-dodecenyl, 5-dodecenyl, 6-dodecenyl, 7-dodecenyl, 8-dodecenyl, 9-dodecenyl, 10-dodecenyl, 11-dodecenyl, 1-tridecenyl, 2-tridecenyl, 3-tridecenyl, 4-tridecenyl, 5-tridecenyl, 6-tridecenyl, 7-tridecenyl, 8-tridecenyl, 9-tridecenyl, 10-tridecenyl, 11-tridecenyl, 12-tridecenyl, 1-tetradecenyl, 2-tetradecenyl, 3-tetradecenyl, 4-tetradecenyl, 5-tetradecenyl, 6-tetradecenyl, 7-tetradecenyl, 8-tetradecenyl, 9-tetradecenyl, 10-tetradecenyl, 11-tetradecenyl, 12-tetradecenyl, 13-tetradeceny, 1-pentadecenyl, 2-pentadecenyl, 3-pentadecenyl, 4-pentadecenyl, 5-pentadecenyl, 6-pentadecenyl, 7-pentadecenyl, 8-pentadecenyl, 9-pentadecenyl, 10-pentadecenyl, 11-pentadecenyl, 12-pentadecenyl, 13-pentadecenyl, 14-pentadecenyl; "alkoxy" can include methoxy, ethoxy, propoxy, isopropoxy, butoxy, iso-butoxy, sec-butoxy, pentoxy, 3-pentoxy, hexoxy, heptyloxy, octyloxy, nonyloxy, decyloxy, undecyloxy, dodecyloxy, tridecyloxy, tetradecyloxy, or pentadecyloxy; "alkanoyl" can include acetyl, propanoyl, butanoyl, pentanoyl, hexanoyl, heptanoyl, octanoyl, nonanoyl, decanoyl, undecanoyl, dodecanoyl, tridecanoyl, tetradecanoyl, or pentadecanoyl; "cycloalkyl" can include cyclopropyl, cyclobutyl, cyclopentyl, cyclohexyl, cycloheptyl, or cyclooctyl. "Aryl" can include phenyl, indenyl, 5,6,7,8-tetrahydronaphthyl, or naphthyl. "Heteroaryl" can include furyl, imidazolyl, tetrazolyl, pyridyl, (or its N-oxide), thienyl, pyrimidinyl (or its N-oxide), indolyl, or quinolyl (or its N-oxide).

Specific independent values for $R_{1-5}$, include alkyl, alkenyl, alkynyl, cycloalkyl, cycloalkyl($C_1$–$C_{10}$)alkyl, ($C_3$–$C_8$)cycloalkyl($C_1$–$C_{15}$)alkenyl, ($C_3$–$C_8$)cycloalkyl ($C_1$–$C_{15}$)alkynyl, ($C_1$–$C_{15}$)alkoxy, ($C_1$–$C_{15}$)alkanoyl, or ($C_1$–$C_{15}$)alkanoyloxy; wherein $R^1$ is optionally substituted with one or more (e.g., 1, 2, 3, or 4) substituents independently selected from the group consisting of halo, nitro, cyano, hydroxy, trifluoromethyl, trifluoromethoxy, ($C_1$–$C_{15}$) alkyl, ($C_2$–$C_{15}$)alkenyl, ($C_2$–$C_{15}$)alkynyl, ($C_3$–$C_8$) cycloalkyl, ($C_3$–$C_8$)cycloalkyl, ($C_1$–$C_{15}$)alkyl, ($C_3$–$C_8$) cycloalkyl-($C_2$–$C_{15}$)alkenyl, ($C_3$–$C_8$)cycloalky($C_2$–$C_{15}$) alkynyl, ($C_1$–$C_{15}$)alkoxy, ($C_1$–$C_{15}$)alkanoyl, ($C_1$–$C_{15}$) alkanoyloxy, C(=O)OR$_a$, C(=O)NR$_b$R$_c$, OC(=O)OR$_a$, OC(=O)NR$_b$R$_c$, AND NR$_e$R$_f$.

Other specific values for $R_{1-5}$ include aryl optionally substituted with 1, 2, or 3 substituents independently selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl, ($C_1$–$C_6$)alkyl, ($C_1$–$C_{10}$)alkoxy, ($C_1$–$C_{10}$)alkanoyl, ($C_2$–$C_{10}$)alkanoyloxy, C(=O)OR$_a$, C(=O)NR$_b$R$_c$, or NR$_e$R$_f$.

Other specific values for $R_{1-5}$, include independently phenyl or naphthyl, optionally substituted with a substituent selected from the group consisting of halo, nitro, cyano, hydroxy, trifluoromethyl, trifluoromethoxy, ($C_1$–$C_6$)alkyl, ($C_2$–$C_{10}$)alkenyl, ($C_2$–$C_{10}$)alkynyl, ($C_3$–$C_8$)cycloalkyl, ($C_3$–$C_8$)cycloalkyl($C_1$–$C_6$)alkyl, ($C_1$–$C_{10}$)alkoxy, ($C_1$–$C_{10}$) alkanoyl, ($C_2$–$C_{10}$)alkanoyloxy, C(=O)OR$_a$, C(=O) NR$_b$R$_c$, or NR$_e$R$_f$.

Still other specific values for $R_{1-5}$, include aryl, heteroaryl, aryl($C_1$–$C_6$)alkyl, heteroaryl($C_1$–$C_6$)alkyl, aryl ($C_2$–$C_6$)alkenyl, heteroaryl($C_2$–$C_6$)alkenyl, aryl($C_2$–$C_6$) alkynyl, or heteroaryl($C_2$–$C_6$)alkynyl; wherein any aryl or heteroaryl is optionally substituted with halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_1$–$C_{15}$)alkyl, ($C_3$–$C_8$)cycloalkyl-($C_2$–$C_{15}$)alkenyl, ($C_3$–$C_8$)cycloalkyl($C_2$–$C_{15}$)alkynyl, ($C_1$–$C_{15}$)alkoxy, ($C_1$–$C_{15}$)alkanoyl, ($C_1$–$C_{15}$)alkanoyloxy, C(=O)$OR_a$, C(=O)$NR_bR_c$, or $NR_eR_f$.

Some examples of $C_3$-substituted and/or $C_4$-substituted derivatives of the subject invention are shown in FIGS. 3A–3H, 11A–11I, 15, and 16A–16D. FIGS. 16A–16D show various $C_3$-sulfonate derivatives having sulfonic acid or benzene-sulfonic acid moieties.

The compounds of the present invention exhibit broad antibacterial activity against several families of bacteria in the Gram-negative and Gram-positive range, and against beta-lactamase formers. Because of their powerful antibacterial properties, the present compounds may also be used to supplement feed for animals.

In addition, the compounds of the present invention that exhibit antibacterial activity may also be used as medicaments, and also as substances for preserving inorganic and organic materials, especially organic materials of all kinds, for example, polymers, lubricants, paints, fibers, leather, paper, timber, foodstuffs, and water. For example, these compounds can be covalently bonded to the polymer.

The compounds of the present invention may also be used to prevent, alleviate, or cure diseases caused by pathogens whose growth is inhibited by these compounds. The instant compounds are particularly active against bacteria and bacteria-like microorganisms. They are therefore suitable for use in human and veterinary medicine, for the prophylaxis and chemotherapy of local and systemic infections caused by these pathogens.

As an illustrative, but not limiting, list of pathogens, the following pathogenic microorganisms are possible targets of the compounds of the present invention. Micrococcaceae, such as *Staphylococci*, for example *Staphylococcus aureus*, *Staph. Epidermidis* and *Staph. Aerogenes*; Lactobacteriaceae, such as *Streptococci*, for example *Streptococcus pyogenes*; Neisseriaceae, such as *Neisseriae*, for example *Neisseria gonorrhoeae* (*Gonococci*); Corynebacteriaceae, such as *Corynebacteria*; *Listeria* bacteria; Erysipelothrix bacteria; *Kurthia* bacteria; Enterobacteriaceae, such as *Escherichia* bacteria of the *Coli* group; *Klebsiella* bacteria; *Erwiniae*; *Serratia*; *Proteae* bacteria; *Providencia* bacteria; *Salmonella* bacteria; *Shigella*; Pseudomonadaceae; *Aeromonas* bacteria; Spirillaceae, such as *Vibrio* bacteria; *Spirillum* bacteria; Parvobacteriaseae; *Brucella* bacteria; *Bordetella* bacteria; *Moraxella* bacteria; *Fusiform* bacteria; Bacillaceae; *Clostridia*; Spirochaetaceae; *Treponema* bacteria; and *Leptospira* bacteria.

Examples which may be cited of diseases which can be prevented, alleviated, or cured by the compounds of the present invention are: diseases of the respiratory passages and of the pharyngeal cavity; otitis; pharyngitis; pneumonia; peritonitis; pyelonephritis; cystitis; endocarditis; systemic infections; and bronchitis.

The compounds of the present invention include all hydrates and salts that can be prepared by those of skill in the art. Under conditions where the compounds of the present invention are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of the present invention can be formulated as pharmaceutical compositions and administered to a patient, such as a human patient, in a variety of forms adapted to the chosen route of administration, i.e., orally or parenterally, by intravenous, intramuscular, topical, or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water or other suitable solvent, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient presenting the previously sterile-filtered solutions.

For topical administration, the present compounds may be applied in pure-form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from adsorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are disclosed in Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art (U.S. Pat. No. 4,938,949 (Borch et al.)).

Generally, the concentration of the compound(s) of formula (I) in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

Accordingly, the invention includes a pharmaceutical composition comprising a compound of the present invention as described above; or a pharmaceutically acceptable salt thereof, in combination with a pharmaceutically acceptable carrier. Pharmaceutical compositions adapted for oral, topical or parenteral administration, comprising an amount of one or more compounds effective to treat a bacterial infection, are a preferred embodiment of the invention.

The present invention provides a novel class of monocyclic substituted β-lactams, specifically termed N-1 thiolated monolactams as defined herein. The present invention will therefore be fully understood by one of skill in the art by reference to the following embodiments, examples, and claims.

EXAMPLE 1

In this study, a selection of N-methylthio-substituted β-lactams are examined for antimicrobial activity by the Kirby-Bauer disk diffusion method on agar plates. A variety of common Gram-positive and Gram-negative bacteria are tested, including clinical isolates of methicillin-resistant *Staphylococcus aureus* (MRSA). See FIGS. 1A–1I.

Compound susceptibility measurements are obtained from agar disk diffusion experiments using 6-mm air-dried disks impregnated with 20 μg of the test compound. The values correspond to the average diameters in mm (triplicate experiments) for the zone of growth inhibition observed after 24 h. *Staphylococcus aureus* (ATCC 25923) and β-lactamase-producing strains of methicillin-resistant *Staphylococcus aureus* (labeled as MRSA USF652–659) are obtained from Lakeland Regional Medical Center, Lakeland, Fla. *Staphylococcus epidermidis, Staphylococcus simulans, Staphylococcus simulans*, and *Microcossus luteus* are clinical isolates from University of South Florida Medical Clinic. *Nieserria gonnorhoeae* (β-lactamase positive) is obtained from the Tampa Branch State Laboratory. PenG is penicillin G (potassium salt). Table 1 provides the zones of growth inhibition that are observed after 24 hours using the lactams of FIGS. 1A–1I (designated A–I, respectively).

TABLE 1

| Bacterial Strain | A | B | C | D | E | F | G | H | I | PenG |
|---|---|---|---|---|---|---|---|---|---|---|
| S. aureus (ATCC 25923) | 27 | 18 | 25 | 26 | 15 | 12 | 14 | 23 | 27 | 34 |
| MRSA USF652 | 31 | 19 | 30 | 30 | 17 | 12 | 14 | 23 | 28 | 8 |
| MRSA USF653 | 30 | 23 | 30 | 30 | 22 | 14 | 16 | 27 | 28 | 16 |
| MRSA USF654 | 28 | 16 | 26 | 26 | 16 | 12 | 12 | 23 | 27 | 10 |
| MRSA USF655 | 29 | 17 | 25 | 26 | 14 | 14 | 12 | 23 | 29 | 14 |
| MRSA USF656 | 30 | 19 | 28 | 28 | 18 | 11 | 13 | 25 | 28 | 12 |
| MRSA USF657 | 30 | 17 | 27 | 28 | 18 | 12 | 10 | 23 | 26 | 12 |
| MRSA USF658 | 27 | 16 | 26 | 27 | 17 | 12 | 12 | 22 | 26 | 19 |
| MRSA USF659 | 25 | 15 | 24 | 24 | 11 | 13 | 12 | 20 | 24 | 15 |
| S. epidermidis | 30 | 23 | 31 | 29 | 20 | 12 | 20 | 25 | 28 | 50 |
| S. simulans (ATCC 11631) | 21 | 11 | 14 | 16 | 13 | 0 | 0 | 14 | 0 | 13 |
| S. saprophyticus (ATCC 3552) | 22 | 12 | 22 | 20 | 15 | 8 | 14 | 15 | 20 | 30 |
| M. luteus | 23 | 20 | 21 | 24 | 22 | 20 | 21 | 21 | 15 | 40 |
| N. gonorrhoeae | 13 | 11 | 14 | 19 | 12 | 11 | 12 | 12 | 11 | 0 |

Table 1: Small zones (<15 mm) were observed against *Bacteroides fragalis* and *Haemophilus influenzae* 561. No zones were observed against *Klebsiella pneumoniae* 512, *Listeria monocytogenes, Vibrio cholorae* 1018 (CDC E5906, toxin+), *Vibrio cholorae* 1019 (CDC 1074–78, toxin−), *Streptococcus pyrogenes* (GAS), *Streptococcus agalactiae* (GBS), *Serratia marcessens* 519 (ATCC 29634), *Salmonella typhimurium* 515, *Pseudomonas aeruginosa* (ATCC 15442), *Proteus mirabilis, Mycobacterium smegmatis, Enterobactor cloacae*, or *Escherichia coli* (ATCC 23590).

The data indicate that the lactams of FIGS. 1A–1I are most active against *Staphylococcus* and *Micrococcus* bacteria, but act only weakly against *Neisseria gonorrhoeae*,

*Bacteroides fragalis*, and *Haemophilus influenzae*. The compounds have no activity against other common microorganisms we examined, including *Klebsiella pneumoniae, Listeria monocytogenes, Vibrio cholorae, Streptococcus pyrogenes* (GAS), *Streptococcus agalactiae* (GBS), *Serratia marcessens, Salmonella typhimurium, Pseudomonas aeruginosa, Proteus mirabilis, Mycobacterium smegmatis, Enterobactor cloacae*, or *Escherichia coli*. Thus, the lactams provide a narrow-spectrum of antibacterial activity, with high selectivity for *Staphylococcus* strains. Most intriguing is the observation that the lactams retain their full effectiveness against the β-lactamase producing MRSA mutants.

Figure 1D:
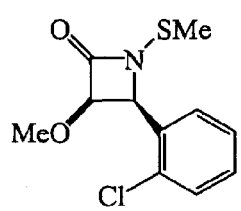
Figure 1E:
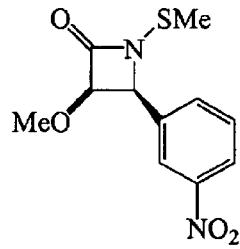
Figure 1F:
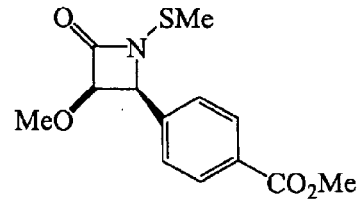
Figure 1G:
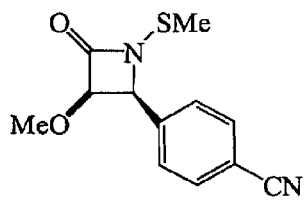
Figure 1H:
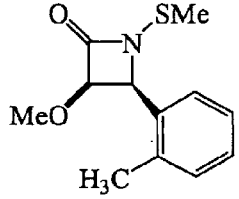
Figure 1I:
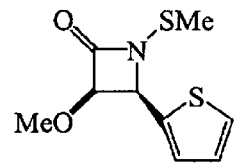

Preliminary structure-activity profiling of these active analogues suggests that the β-lactam ring can carry a wide variety of unsaturated substituents at the $C_4$ center, including alkynyl, alkenyl, aryl, or heteroaryl moieties. However, the N-alkylthio substituent is required, since reduction to the N—H analogue completely destroys the biological activity. Minimum inhibitory concentration (MIC) values for the lactam of FIG. 1D, the most active analogue among the nine studied, are determined from agar dilution experiments (the low water solubility of the lactams hampered our attempts to reliably measure the MIC values using the standard broth turbidity test by serial dilution) to be 15 μg/mL for *Staphylococcus aureus* and 5–10 μg/mL for the MRSA strains. The lactam of FIG. 1D is considerably more active in controlling MRSA than penicillin, whose MIC's are >64 μg/mL.

The structure-bioactivity patterns observed for these N-thiolated lactams are highly atypical for a β-lactam antibiotic. The compounds are lipohilic and devoid of the typical acidic ring functionality required for recognition by the penicillin binding proteins. The implication that the lactams set forth in FIGS. 1A–1I are not acting in the same manner or on the same enzymes as the traditional β-lactam drugs is supported by electron microscopy experiments, which confirm that cell morphology is unaffected by the lactam of FIG. 1D (Greenwood, D. et al. *Science*, 1969, 163:1076).

Whereas cells grown in the presence of penicillin G or vancomycin (inhibitors of cell wall biosynthesis) appear wrinkled, deformed, or even sheared upon high magnification, and take on a pink coloration upon Gram staining (Lorian, V. and C. G. Gemmell, In *Antibiotics in Laboratory Medicine*, 3rd ed.; Williams and Wilkins: Baltimore, 1991; Chapter 14), those treated with the lactam of FIG. 1D display no visible damage or morphological deformities. In fact, only small isolated colonies of surviving cells can be found, all of which appear perfectly normal in size, shape, smoothness, and clustering behavior. Gram staining of these cluster of colonies produces a uniform purple coloration indicative of cells having a fully formed and intact cell wall (identical to that of untreated cells). The complete absence of any deformed, fused, folded or pink-stained cells (after staining) within these colonies indicates that the lactam of FIG. 1D is not altering cell wall cross-linking. Pulse radiolabeling experiments indicate that the lactam of FIG. 1D blocks the bacterial uptake of $^3$H-uridine and $^3$H-leucine at low (MIC) levels (Lim, D. V. et al. *Microbiology*, 1977, 33:328; Champney, W. S. and C. G. Tober *Antimicrob. Agents and Chemother.*, 2000, 44:1413).

The fact that the compounds of FIG. 1A–1I retain their full antibacterial activity against β-lactamase-producing strains of MRSA suggests that these lactams are unaffected by bacterial penicillinases. In vitro experiments confirm that the lactams of FIGS. 1A–1I are indeed hydrolytically-resistant to penicillinases for prolonged periods, and that they do not inhibit β-lactamase-induced cleavage of penicillin G. Thus, the compounds appear to be transparent to β-lactamase proteins. Moreover, the resilience these β-lactams have toward β-lactamases and the unprecedented structure-activity patterns, (the antimicrobial activity of these-lactams is in sharp contrast to the lack of antibacterial properties of the thiamazins, N—SCH$_2$CO$_2$H β-lactams, which are the closest structural analogues (Woulfe, S. R. and M. J. Miller *J. Org. Chem.*, 1986, 51:3133; Boyd, D. B. et al. *J. Med. Chem.*, 1987, 30:528) the display supports the hypothesis that the compounds are operating through a unique mode of action. Preliminary experiments indicate that the lactams are not cytotoxic to healthy mammalian cells (human fibroblasts) at concentrations more than three times the bacterial MIC's.

Table 2 provides selected characterization data for the lactams of FIGS. 1A–1I, designated in Table 2 as lactams A–I, respectively.

TABLE 2

| Lactam | MP | $^1$H NMR data |
|---|---|---|
| A | 74–76° C. | δ 7.42 (d, J = 8.8 Hz, 2H), 7.30 (m, 3H), 4.72 (d, J = 4.8 Hz, 1H), 4.63 (d, J = 4.8 Hz, 1H), 3.56 (s, 3H), 2.58 (s, 3H) |
| B | 92–94° C. | δ 7.31 (m, 5H), 6.80 (d, J = 15.8 Hz, 1H), 6.25 (dd, J = 15.8, 9.4 Hz, 1H), 4.70 (d, J = 4.7 Hz, 1H), 4.41 (dd, J = 9.4, 4.7 Hz, 1H), 3.48 (s, 3H), 2.44 (s, 3H) |
| C | 51–54° C. | δ 7.31 (m, 5H), 4.76 (d, J = 4.9 Hz, 1H), 4.72 (d, J = 4.9 Hz, 1H), 3.08 (s, 3H), 2.29 (s, 3H) |
| D | 71–73° C. | δ 7.35 (d, J = 7.4 Hz, 1H), 7.24 (m, 3H), 5.29 (d, J = 4.9 Hz, 1H), 4.80 (d, J = 4.9 Hz, 1H), 3.16 (s, 3H), 2.40 (s, 3H) |
| E | Oil | δ 8.25 (ABm, 2H), 7.71 (d, J = 7.3 Hz, 1H), 7.61 (t, J = 7.7 Hz, 1H), 4.96 (d, J = 5.0 Hz, 1H), 4.85 (d, J = 5.0 Hz, 1H), 3.25 (s, 3H), 2.42 (s, 3H) |
| F | 106–107° C. | δ 8.06 (d, J = 8.2 Hz, 2H), 7.43 (d, J = 8.2 Hz, 2H), 4.88 (d, J = 4.9 Hz, 1H), 4.81 (d, J = 4.9 Hz, 1H), 3.92 (s, 3H), 3.15 (s, 3H), 2.37 (s, 3H) |
| G | 88–90° C. | δ 7.64 (d, J = 8.0 Hz, 2H), 7.40 (d, J = 8.0 Hz, 2H), 4.79 (ABm, 2H), 3.14 (s, 3H), 2.37 (s, 3H) |
| H | 80–81° C. | δ 7.23 (m, 4H), 5.11 (d, J = 5.0 Hz, 1H), 4.85 (d, J = 5.0 Hz, 1H), 3.21 (s, 3H), 2.45 (s, 3H), 2.37 (s, 3H) |
| I | Oil | δ 7.43 (d, J = 5.0 Hz, 1H), 7.21 (d, J = 2.9 Hz, 1H), 7.06 (dd, J = 5.0, 2.9 Hz, 1H), 5.08 (d, J = 4.7 Hz, 1H), 4.82 (d, J = 4.8 Hz, 1H), 3.32 (s, 3H), 2.30 (s, 3H) |

EXAMPLE 2

Probing the Effect of Unsaturation in the $C_4$ Side Chain of N-Thiolated β-Lactam Antibacterials This example is directed to the effect of unsaturation in the C-4 side chain on antibacterial activity of lactams set forth in FIGS. 2A–2D. The recent discovery of a novel family of antibacterial agents comprised of structure 1 below,

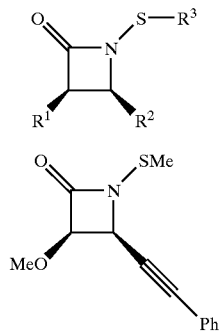

has shown for the first time that a β-lactam molecule need not possess ionic or acidic ring residues to have antimicrobial activity (Turos, E. et al. *Tetrahedron*, 2000, 56:5571). This is demonstrated most convincingly with the N-methylthio lactam of structure 2, whose antimicrobial activity appears to be enhanced against β-lactamase producing strains of methicillin-resistant *Staphylococcus aureus* (MRSA) over other common microorganisms. The structure and antimicrobial effects of this highly lipophilic compound are completely different to those of all other β-lactam antibiotics, which carry ionic or acidic functionality close to the lactam carbonyl in order to be recognized by penicillin binding proteins (Long, T. E. and E. Turos, *Curr. Med. Chem. -Anti-Infective Agents*, 2002, 1:251–268; Turos, E. et al., *Bioorganic & Medicinal Chemistry Letters*, 2002, 12:2229–2231; *Chemistry and Biology of β-Lactam Antibiotics*; Morin, R. B. and M. Gorman, Eds., Academic Press: New York, 1982, Volumes 1–3). Further investigations on this exciting new class of antimicrobial agents are directed to determine their mode of action, and the structural features responsible for their biological activity.

Figure 2A:
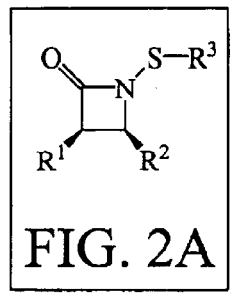
FIGS. 2A–2D show N-Methylthio β-lactam antibacterials.
Figure 2B:
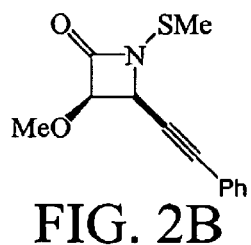
Figure 2B:
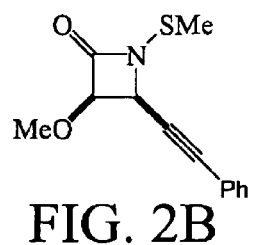
Figure 2C:
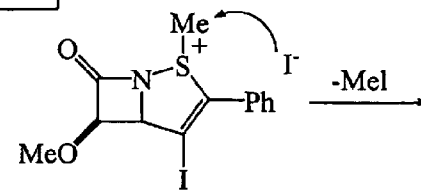

Referring to FIGS. 2A–2D, the lactam of FIG. 2B undergoes cyclization to isopenem (FIG. 2D) when exposed to molecular iodine in organic media (*Recent Progress in the Chemical Synthesis of Antibiotics*, Kukacs, F.; Ohno, M., Eds.; Springer-Verlag: Berlin-Heidelberg, (1990); Ren, X.-F. et al. *J. Org. Chem.*, 1998, 63:8898). The putative intermediate in this transformation, bicyclo sulfonium species (FIG. 2C), acts as a potent alkylating agent by transferring its S-methyl group to iodide ion (Ren, X.-F. et al. *E. J. Org. Chem.*, 1995, 60:4980. Screenings show that the product of this reaction, the bicyclic lactam of FIG. 2D, has no antimicrobial activity. However, not to be limited by theory, it is envisioned that a similar type of cyclization-dealkylation process could possibly be occurring in vitro to account for the biological activity of the monocyclic lactam (FIG. 2B). Namely, a biological electrophile could activate the monocyclic lactam of FIG. 2B toward heterocyclization, leading to the formation of a reactive alkylating agent (similar to that of FIG. 2C) that inactivates a susceptible biological nucleophile vital to bacterial cell growth.

Figure 2D:
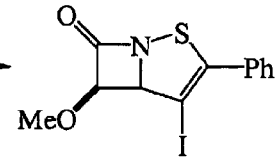

To test this possibility, a series of structurally related $C_4$-substituted lactams (those of FIGS. 3A–3H) were prepared and screened for antibacterial activity, along with the lactams of FIGS. 2B and 2D.

Of particular interest is the ability of these compounds to retain their effectiveness against penicillin-resistant strains of *Staphylococcus aureus*, a dangerous hospital-borne pathogen which is becoming difficult to treat with conventional antibiotic therapy. The lactams were screened for antibacterial activity by disk diffusion on agar plates, and the resulting zones of bacterial growth inhibition measured (see Table 3; each lactam is designated by Figure number).

TABLE 3

| Microorganism | 2B | 2D | 3A | 3B | 3C | 3D | 3E | 3F | 3G | 3H | PenG |
|---|---|---|---|---|---|---|---|---|---|---|---|
| *Staphylococcus aureus* (ATCC 25923) | 27 | 0 | 10 | 21 | 15 | 15 | 16 | 17 | 14 | 0 | 34 |
| MRSA USF652 | 29 | 0 | 10 | 25 | 18 | 14 | 18 | 17 | 14 | 0 | 8 |
| MRSA USF653 | 29 | 0 | 18 | 26 | 18 | 16 | 20 | 18 | 12 | 0 | 16 |
| MRSA USF654 | 27 | 0 | 12 | 22 | 16 | 14 | 17 | 17 | 13 | 0 | 10 |
| MRSA USF655 | 27 | 0 | 12 | 21 | 18 | 15 | 15 | 15 | 11 | 0 | 14 |
| MRSA USF656 | 30 | 0 | 13 | 24 | 17 | 13 | 17 | 18 | 13 | 0 | 12 |
| MRSA USF657 | 28 | 0 | 11 | 22 | 16 | 13 | 14 | 17 | 12 | 0 | 12 |
| MRSA USF658 | 27 | 0 | 10 | 21 | 16 | 12 | 15 | 15 | 12 | 0 | 19 |
| MRSA USF659 | 24 | 0 | 10 | 17 | 15 | 12 | 15 | 16 | 12 | 0 | 15 |
| *Staphylococcus simulans* | 19 | 0 | 9 | 12 | 10 | 8 | 9 | 11 | 8 | 0 | 13 |
| *Staphylococcus saprophyticus* | 23 | 0 | 14 | 16 | 12 | 11 | 9 | 13 | 10 | 0 | 30 |
| *Staphylococcus epidermidis* | 30 | 0 | 12 | 26 | 19 | 10 | 12 | 18 | 12 | 0 | 50 |
| *Micrococcus luteus* | 28 | 0 | 11 | 23 | 17 | 10 | 20 | 23 | 17 | 0 | 40 |

Table 3: Growth inhibition zones obtained from agar disk diffusion experiments using 6-mm air-dried disks impregnated with 20 μg of the test compound. The values correspond to the average diameters in mm for the zone of growth inhibition observed after 24 hours. *Staphylococcus aureus* and β-lactamase-producing strains of methicillin-resistant *Staphylococcus aureus* (labeled MRSA USF652–659) are obtained from a clinical testing laboratory at Lakeland Regional Medical Center, Lakeland, Fla.

There are several important conclusions that can be made in light of this data. First, all four of the $C_4$-alkenyl-substituted lactams shown in FIGS. 3A–3D are active against the MRSA isolates as well as the other microbes tested, although their zones of growth inhibition are somewhat smaller than those of the parent alkynyl analogue shown in FIG. 2B. It is also interesting that the Z-compound (FIG. 3B) produces much larger inhibition zones than the corresponding E-isomer (FIG. 3A), indicating that olefin geometry can be a contributing factor to biological performance. Within this alkenyl series, the $C_3$-methoxy lactam shown in FIG. 3A and the $C_3$-acetoxy compound shown in FIG. 3C are slightly more active than the $C_3$-phenoxy derivative (FIG. 3D) on an equal weight basis (20 μg/disk). Perhaps the most surprising results are those of the three alkyl derivatives (FIGS. 3E–3G), which are consistently more active than the alkenyl analogues. This offers convincing evidence that unsaturation in the $C_4$-side chain of these N-methylthio lactams is not a requirement for antimicrobial activity, and that bioactivation of the molecule according to the mechanism suggested above is unnecessary. Furthermore, the fact that the propargylic lactam shown in FIG. 3H is inactive against all the microorganisms tested suggests that there is perhaps a more subtly structural basis for the microbiological activity within this class of β-lactams. This study provides important information into the design of new lactam analogues for treatment of MRSA infection.

EXAMPLE 3

N-Thiolated β-Lactams: Structurally and Mechanistically Novel Antibacterial Agents for MRSA Early profiling of N-Thiolated β-lactams 1

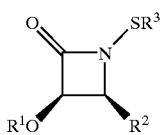

has revealed highly unusual structure-activity trends and a mode of action that is different to that of any current β-lactam antibiotic. Unlike penicillin and other traditional β-lactam drugs these compounds do not block bacterial cell growth by inhibiting cell wall cross-linking or penicillin binding proteins. Not to be limited by theory, experiments indicate that the lactams affect early developmental events within the cytoplasm of the cell. FIG. 4 illustrates common β-Lactam Antibiotics.

Figure 5:
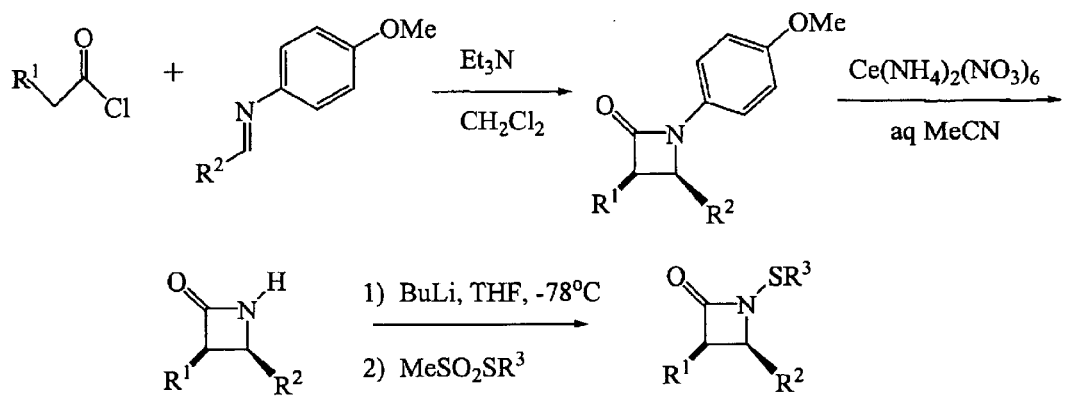
FIG. 5 shows synthesis of N-Thiolated β-Lactams.

SAR studies were initiated by preparing analogues differing in the three ring substituents $R^1$, $R^2$, and $R^3$. These N-thiolated β-lactam antibacterials were prepared in a single step from N-protio lactams. Synthesis of N-Thiolated β-Lactams is illustrated in FIG. 5. Most N—H lactam variants are prepared in two steps: (1) Staudinger coupling of an acid chloride with an N-(4-methoxyphenyl)imine, followed by (2) N-dearylation with ceric ammonium nitrate.

Figure 6A:
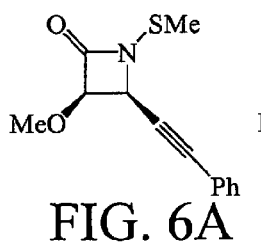
FIGS. 6A–6J show N-Methylthio β-lactam antibacterials.
Figure 6B:
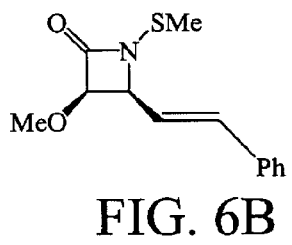
Figure 6C:
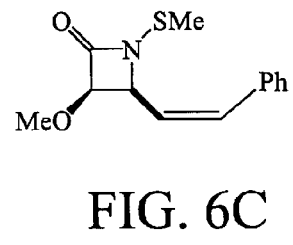
Figure 6D:
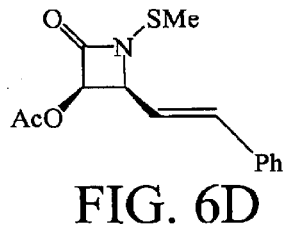
Figure 6E:
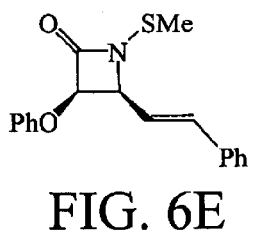
Figure 6F:
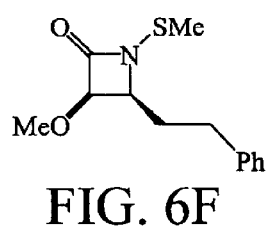
Figures 6G, 6H:
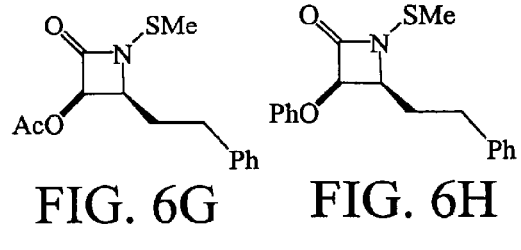
Figure 6I:
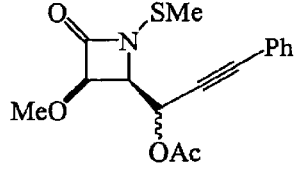
Figure 6J:
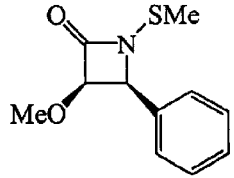

Compounds studied in this series of experiments are set forth in FIGS. 6A–6J. The first compound studied, the β-lactam shown in FIG. 6A, inhibits the in vitro growth of *Staphylococcus aureus* and other select species of bacteria. Interestingly, biological activity of the β-lactam of FIG. 6A is enhanced against β-lactamase producing strains of methicillin-resistant *Staphylococcus aureus* (MRSA). With the lactam of FIG. 6A serving as a lead structure, other $C_4$-unsaturated derivatives (FIGS. 6B–6E) and $C_4$-saturated analogues (FIGS. 6F–6H), were examined all of which also have activity against *Staphylococcus* strains including MRSA. The compound of FIG. 6I is devoid of activity, but the $C_4$-phenyl substituted system of FIG. 6J is highly active against MRSA.

Given the potent activity of the phenyl analogue shown in FIG. 6J, the influence of aryl ring substitution on antibacterial activity was examined. Halogenated compounds set forth in FIGS. 7A–7J were tested and found to be highly active, regardless of the type of halogen or its location on the phenyl ring. Other substituents such as nitro, methyl, cyano, and ester groups can also be added to the ring without loss of activity.

Figure 8A:
FIGS. 8A–8E show compounds examined to determine the effect of fatty ester chain length on the antimicrobial properties.
Figure 8B:
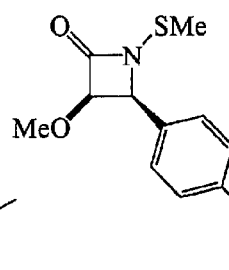
Figure 8C:
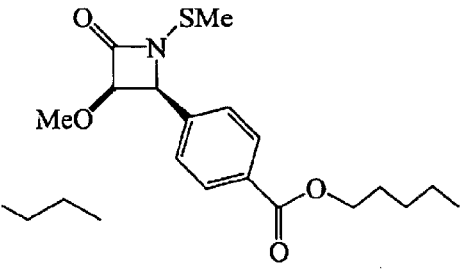
Figure 8D:
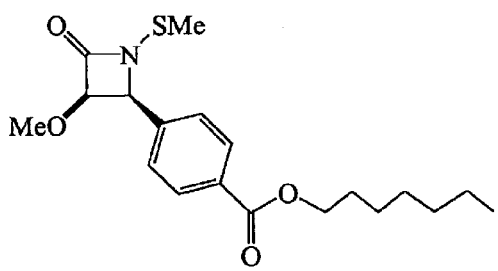
Figure 8E:
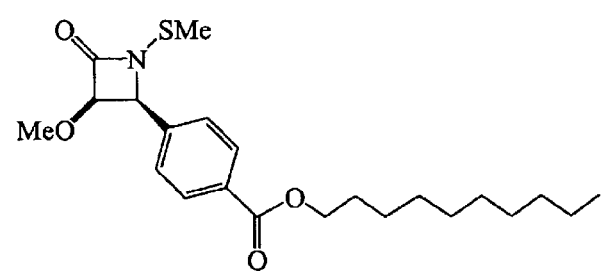
Figure 9A:
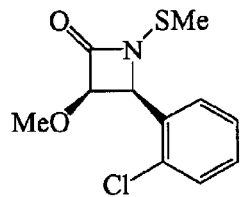
FIGS. 9A–9F show lactams prepared by attachment of various organothio groups differing in chain length or branching.
Figure 9B:
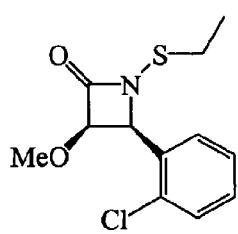
Figure 9C:
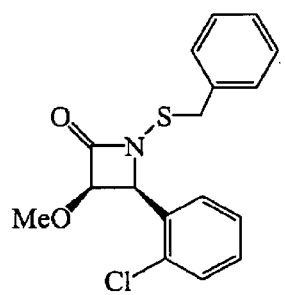
Figure 9D:
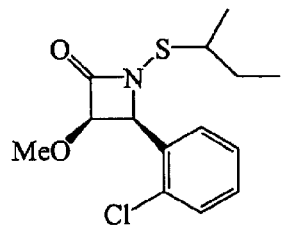
Figure 9E:
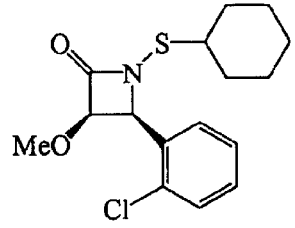
Figure 9F:
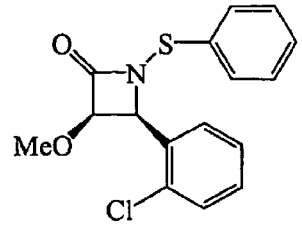
Figure 15:
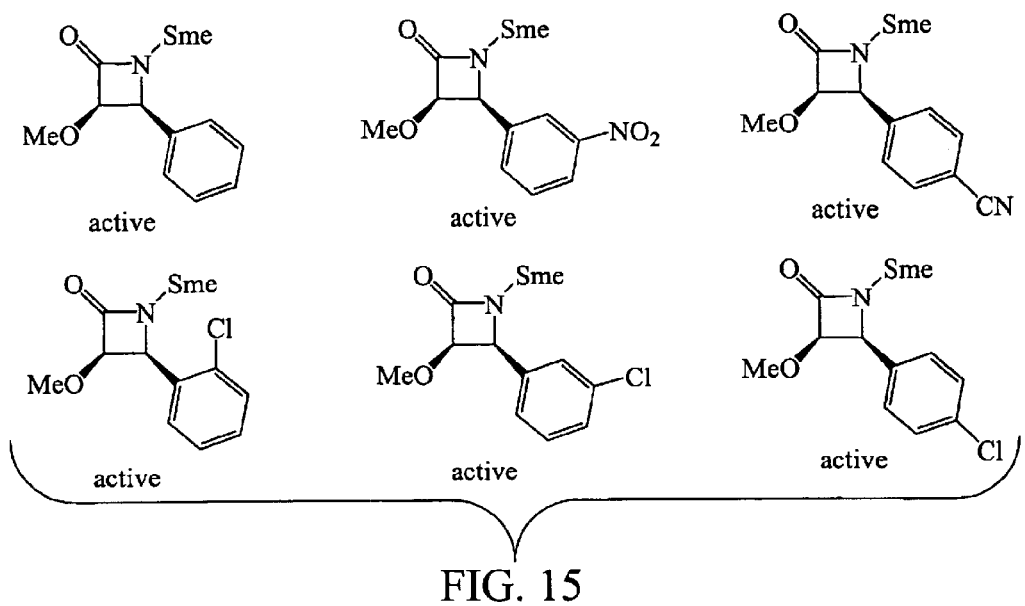
FIG. 15 shows N-methylthio β-lactam antibacterials.

With the methyl ester (FIG. 7J) showing antibacterial activity, compounds of FIGS. 8A–8E are next studied to examine the effect of fatty ester chain length on the antimicrobial properties. It was found that activity is maintained through the pentyl ester (FIG. 8C). However, activity decreases markedly once the ester side chain is longer than five carbons. Thus, heptyl ester (FIG. 8D) has only about half the activity of the pentyl analogues, and decyl ester (FIG. 8E) is totally devoid of activity.

The effect of the organothio moiety on antibacterial activity was also examined by modifying the most active analogue, N-methylthio lactam (FIG. 7A). Lactams set forth in FIGS. 9A–9E were prepared from the same NH intermediate by attachment of various organothio groups differing in chain length or branching. All of these new lactams have antibacterial activity, but bioactivity decreases with increasing chain length and branching. This suggests that biological activity is related to the sterics around the sulfur atom, which appears to be the site of attack by a biological nucleophile.

The N-thiolated β-lactams represent a novel class of β-lactam antibacterials having unique SAR patterns and unusual mode of action. Further studies focus on understanding the biochemical and chemical mechanisms of action of these compounds, and identifying their cellular target. Through further modification and development, these compounds offer a wide range of opportunities for successfully producing therapies for drug-resistant infections.

EXAMPLE 4

Structure-Activity Studies on N-Thiolated β-Lactams: Effect of the Organothio Substituent on Antibacterial Activity The focus of this particular study was to find the role of the N-thioalkyl substituent on the antibacterial properties of N-methylthio-substituted β-lactams. In order to evaluate the role of the organothio moiety (SR) on antibacterial activity in these compounds, a series of analogues were prepared in which the thio substituent is varied. The structure of these analogues is shown below (structure 3), where R is varied from methyl, ethyl, butyl, sec-butyl, cyclohexyl, benzyl, phenyl, and octyl.

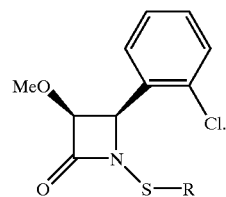

The synthesis of the β-lactams was carried out as described previously, herein. The imine was prepared from ortho-chlorobenzaldehyde, and then used in the Staudinger reaction with methoxyacetyl chloride to afford the β-lactam ring. This compound was then dearylated using ceric ammonium nitrate, and the NH lactam was converted to the N-organothio derivative with the appropriate alkyl thiophthalimide reagent in the presence of catalytic triethylamine.

Those compounds were tested for bioactivity using the Kirby-Bauer test on agar plates. The observed zones of growth inhibition are listed in Table 4. Not to be limited by theory, tested compounds demonstrate that the nature of the organothio group does have a role in antibacterial activity.

TABLE 4

Kirby-Bauer Tests with Zones of Inhibition given
in mm (@ 20 μg disk loading)

| Antibiotic | Staph aureus Strain 525 | MRSA 652 | MRSA 653 | MRSA 654 | MRSA 655 | MRSA 656 | MRSA 657 | MRSA 658 | MRSA 659 |
|---|---|---|---|---|---|---|---|---|---|
| Penicillin | 33 | 8 | 15 | 9 | 14 | 12 | 12 | 19 | 15 |
| Vanco-mycin |  | 19 | 18 | 19 | 19 | 21 | 18 | 18 | 18 |
| Methyl-thio | 26 | 30 | 29 | 26 | 26 | 28 | 27 | 26 | 23 |
| Ethylthio | 26 | 33 | 33 | 27 | 28 | 29 | 29 | 30 | 30 |
| Butylthio | 25 | 26 | 27 | 23 | 23 | 25 | 26 | 20 | 24 |
| sec-Butyl | 32 | 38 | 34 | 35 | 34 | 36 | 33 | 35 | 33 |
| Phenyl | 25 | 18 | 20 | 18 | 18 | 18 | 18 | 22 | 20 |
| Cyclo-hexyl | 21 | 25 | 20 | 21 | 22 | 23 | 23 | 26 | 22 |

However, the majority of the N-thioalkylated β-lactams show greater activity against methicillin resistant *Staphylococcus aureus*, which has reduced susceptibility to either penicillinG or vancomycin. Currently in purification and testing are the N-octylthio, N-methoxythio, and methyl N-glycoxylthio analogues.

EXAMPLE 5

N-Thiolated β-Lactams: A Novel Family of Antibacterial Agents for MRSA

This example describes investigations into the chemical and biological basis for antimicrobial activity of N-Thiolated β-lactams, as well as preliminary SAR and chemical stability studies, and cell microscopy experiments. Unlike penicillin and other traditional β-lactam drugs, these compounds do not inhibit cell wall cross-linking or penicillin binding proteins. (Traditional β-lactam drugs are set forth in FIG. 10). Not to be limited by theory, initial biological studies have revealed the lactams are acting on events within the cytoplasm.

B-lactam 1 inhibits the in vitro growth of *Staphylococcus aureus* an other select species of bacteria. Biological activity is enhanced against β-lactamase producing strains of methicillin-resistant *Staphylococcus aureus* (MRSA). With the lactam shown in FIG. 11A serving as a lead structure, a series of other C-4 substituted derivatives (FIGS. 11B–11I) were investigated herein. Table 5 lists microbiological data for β-lactams from Kirby-Bauer Disc Diffusion Test Results (with each lactam identified by Figure number).

Figure 12:
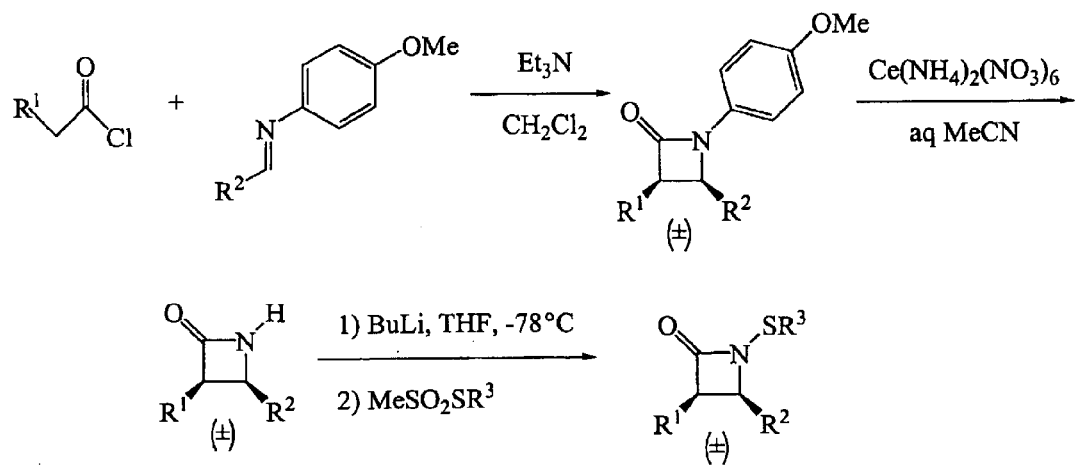
FIG. 12 shows synthesis of N-Thiolated β-Lactams.

These N-thiolated β-lactam antibacterials are prepared in a single step from N-protio lactams (see FIG. 12). Most variants of N—H lactams can be prepared in just two steps: (1) Staudinger coupling of an acid chloride with an N-(4-methoxyphenyl)imine, followed by (2) N-dearylation with ceric ammonium nitrate.

Figure 13C:
FIGS. 13A–13C shows scanning electron microscope images of MRSA on agar (6020× magnification). No antibiotic is present in FIG. 13A. Lactam 6 is present in FIG. 13B. Penicillin G is present in FIG. 13C.
Figure 13B:
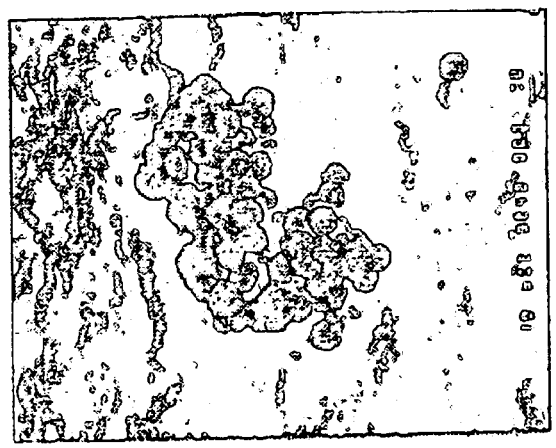
Figure 13A:
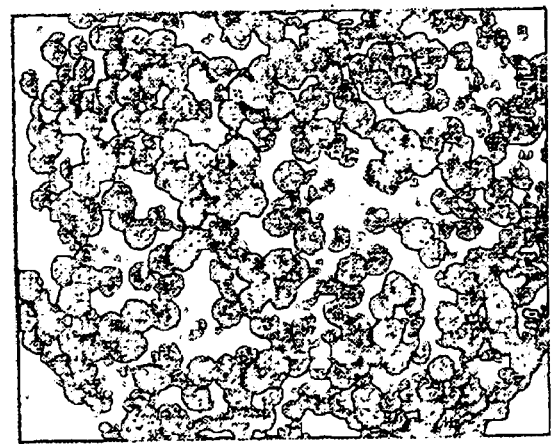

Only certain Gram-positive and Gram-negative bacteria species are susceptible to these lactams, indicating that the biological mechanism of action may not be inhibition of cell wall synthesis. Light microscopy and scanning electron microscopy experiments have enabled us to look for cell wall damage in cultures of *S. aureus* and MRSA grown in the presence of N-methylthio lactam (FIG. 11F) over a range of different concentrations and cell growth conditions. Highly reduced cell counts are generally observed, but in no cases have we found alterations in the shapes or sizes of any of the remaining cells. Those cells that survive the treatment appear normal (coccal) and fully mature. FIG. 13B shows those cells obtained for cultures that have been treated with the lactam shown in FIG. 11F, versus untreated cells (FIG. 13A) and those treated with penicillin (FIG. 13C). The fact that relatively small numbers of colonies of mature, fully intact cells are observed suggests that the lactams may be affecting cellular replication at an early stage, rather than cell wall cross-linking (a late stage event).

Figure 14A:
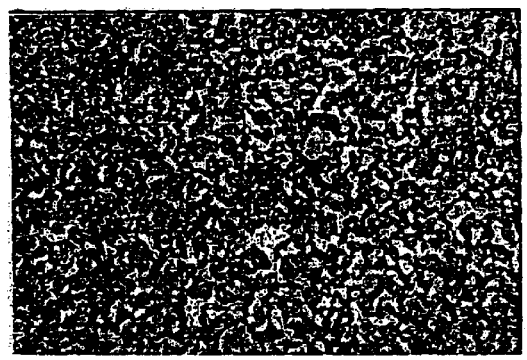
FIGS. 14A–14C shows light microscope photos of MRSA on agar after gram-staining.
Figure 14B:
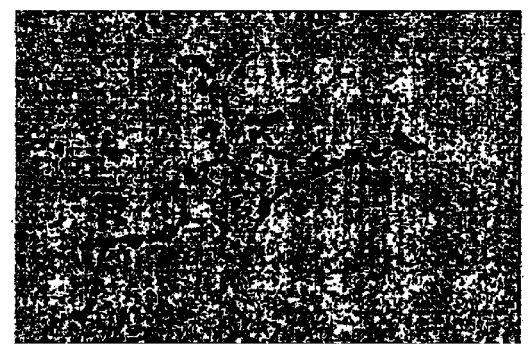
Figure 14C:
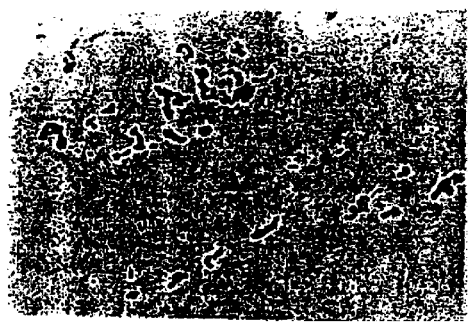
Figure 16A:
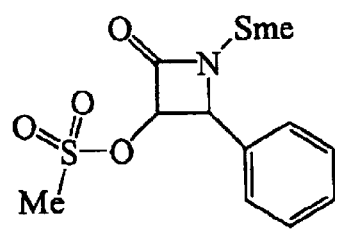
FIGS. 16A–16D show a series of $C_3$-substituted sulfonate derivatives.
Figure 16B:
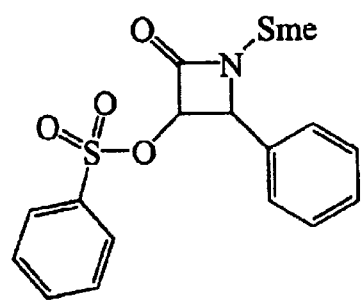
Figure 16C:
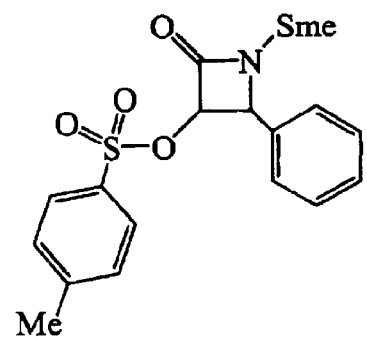
Figure 16D:
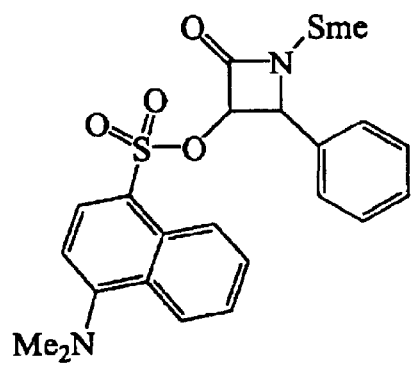

Light microscopy experiments corroborate this suggestion. (FIGS. 14A–14C) *S. aureus* is a Gram-positive microorganism, and thus reacts with Gram stain to produce a purple coloration due to binding of the stain to the peptidoglycan. 100% of MRSA cells grown either in the absence or presence of the lactam of FIG. 11F take on a purple color when Gram stained (top and center images, next

TABLE 5

| Bacteria | 11A | 11B | 11C | 11D | 11E | 11F | 11G | 11H | 11I | Pen | Van |
|---|---|---|---|---|---|---|---|---|---|---|---|
| *S.aureus* 525 | 27 | 25 | 15 | 14 | 27 | 26 | 24 | 24 | 24 | 33 | n/a |
| MRSA 652* | 29 | 30 | 17 | 14 | 28 | 30 | 26 | 24 | 24 | 8 | 19 |
| MRSA 653* | 29 | 30 | 22 | 16 | 28 | 30 | 28 | 28 | 26 | 15 | 18 |
| MRSA 654* | 27 | 26 | 16 | 0 | 27 | 26 | 21 | 23 | 21 | 10 | 19 |
| MRSA 655 | 27 | 26 | 14 | 12 | 29 | 26 | 23 | 23 | 20 | 13 | 19 |
| MRSA 656* | 30 | 28 | 18 | 13 | 28 | 26 | 26 | 22 | 22 | 10 | 21 |
| MRSA 657* | 28 | 28 | 18 | 10 | 26 | 28 | 25 | 22 | 20 | 12 | 18 |
| MRSA 658* | 27 | 27 | 17 | 12 | 26 | 28 | 22 | 20 | 20 | 18 | 18 |
| MRSA 659* | 24 | 24 | 11 | 12 | 24 | 27 | 15 | 18 | 17 | 16 | 18 |

*beta-lactamase producing strains,
Pen = Penicillin G,
Van = Vancomycin page). In contrast, for MRSA cells treated with penicillin G or vancomycin (cell wall synthesis inhibitors), only about 30% of the cells are Gram-stained purple, with the remainder of the cells appearing pink (bottom image, next page) due to morphologically altered walls. This is strong evidence that the N-methylthio lactams are not affecting late stage events in cell wall biosynthesis.

The N-thiolated β-lactams described herein comprises a novel class of synthetically derived β-lactam antibacterials. Through further structural modification and optimization of these lead compounds, new pharmaceuticals can be developed to effectively treat drug-resistant infections.

EXAMPLE 6

Studies on the Influence Fatty Ester Side Chains Have on Antibacterial Activity of N-Thiolated β-Lactams In connection with the ongoing structure-activity studies on N-thiolated β-lactams, a series of benzoate ester derivatives are examined in this series of investigations for antimicrobial activity. The effect of alkyl chain length and branching character of the ester R group in these β-lactams on antibacterial activity is described herein.

As stated, N-Thiolated β-lactams (1) comprise a novel family of antibacterial agents showing enhanced activity against methicillin-resistant *Staphylococcus aureus* (MRSA).

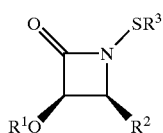
(1)

The C-4 substituted aryl derivatives shown above are found to also be active for MRSA and other *Staphylococcus* microbes. In this example, studies are described on ester-substituted aryl analogues, see FIG. 15.

Scheme I summarizes the synthesis of ester compounds 4. 4-Carboxy benzaldehyde (1) is coupled with the appropriate alcohol using DCC/DMAP, followed by reaction with p-anisidine, to give imines 2. Staudinger coupling of methoxyacetyl chloride with imine 2 gives N-aryl protected β-lactam 3. N-Dearylation of β-lactam 3 with ceric ammonium nitrate and methylthiolation with N-(methylthio) phthalimide affords N-methylthio β-lactams 4. These compounds are tested for antibacterial activity by the Kirby-Bauer method of disc diffusion on agar plates. Table 6 lists the microbiological data for these β-lactams.

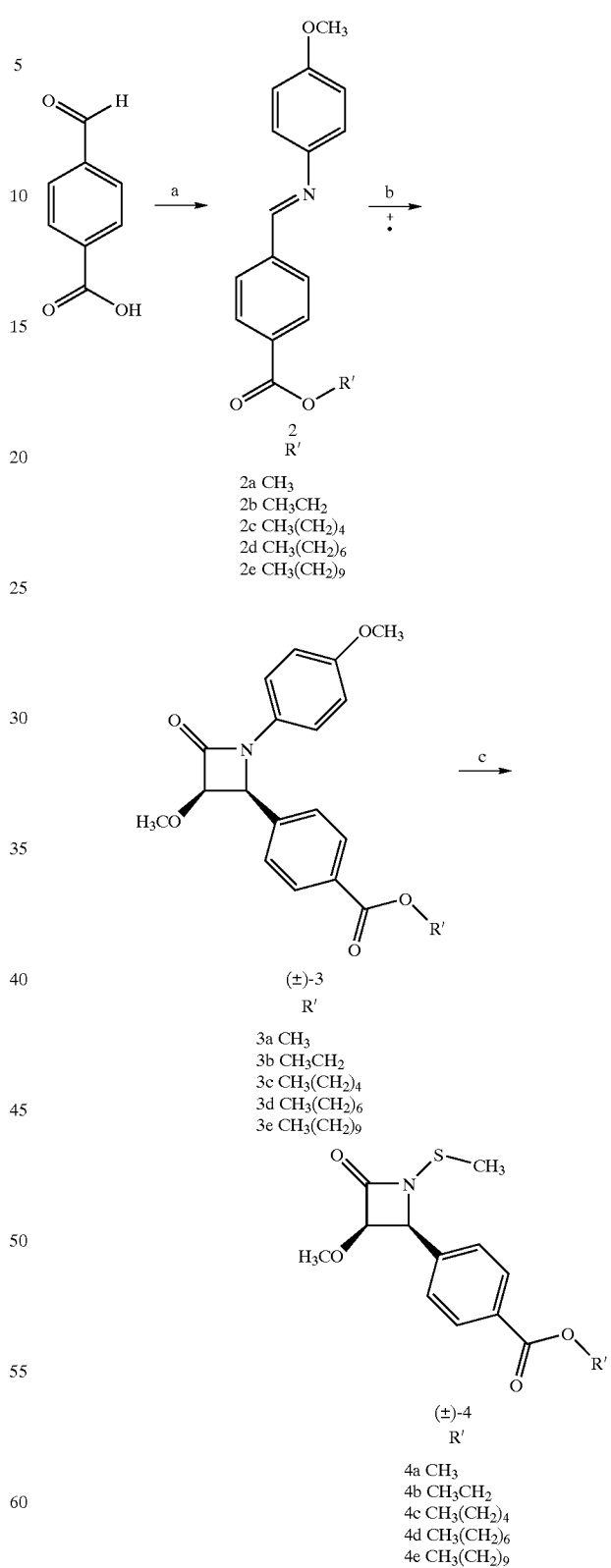

Scheme 1

2
R'
2a CH$_3$
2b CH$_3$CH$_2$
2c CH$_3$(CH$_2$)$_4$
2d CH$_3$(CH$_2$)$_6$
2e CH$_3$(CH$_2$)$_9$ (±)-3
R'
3a CH$_3$
3b CH$_3$CH$_2$
3c CH$_3$(CH$_2$)$_4$
3d CH$_3$(CH$_2$)$_6$
3e CH$_3$(CH$_2$)$_9$ (±)-4
R'
4a CH$_3$
4b CH$_3$CH$_2$
4c CH$_3$(CH$_2$)$_4$
4d CH$_3$(CH$_2$)$_6$
4e CH$_3$(CH$_2$)$_9$

[a]Conditions: (a) (i) R'—OH, DCC, DMAP, dry acetone, reflux; in the case of 2a, CH$_3$OH, SOCl$_2$, 0° C. to room temperature; (ii) p-anisidine, Et$_3$N, CH$_2$Cl$_2$. (b) CH$_3$OCH$_2$COCl, Et$_3$N, CH$_2$Cl$_2$. (c) (NH$_4$)$_2$Ce(NO$_3$)$_6$, CH$_3$CN—H$_2$O; (ii) N-methylthio phthalimide, Et$_3$N, CH$_2$Cl$_2$.

TABLE 6

The Zone of Inhibition (in mm, @20 μg disk loading)

| Strain | 4a | 4b | 4c | 4e | Pen G | Vancomycin |
|---|---|---|---|---|---|---|
| MRSA 652 | 12 | 17 | 17 | 0 | 8 | 23 |
| MRSA 653 | 14 | 14 | 13 | 0 | 15 | 20 |
| MRSA 654 | 8 | 9 | 11 | 0 | 9 | 20 |
| MRSA 655 | 14 | 12 | 13 | 0 | 13 | 19 |
| MRSA 656 | 11 | 11 | 14 | 0 | 10 | 20 |
| MRSA 657 | 12 | 14 | 14 | 0 | 12 | 21 |
| MRSA 658 | 9 | 11 | 12 | 0 | 18 | 20 |
| MRSA 659 | 13 | 13 | 12 | 0 | 16 | 20 |

MRSA: Methicillin-resistant *Staphylococcus aureus*

It is apparent from the observed zones of growth inhibition in Table 6 that β-lactams 4a, 4b, and 4c have about similar activity. However, decyl ester 4e has no activity, indicating that the increasing chain length, if extended long enough, has a detrimental effect on the antibacterial properties.

Ortho-substituted esters such as lactam 8 are also good candidate compounds to study for biological activity. However, it was not possible to synthesize methyl ester corresponding to compound 8, but the ethyl ester is prepared as shown in Scheme II.

Scheme II

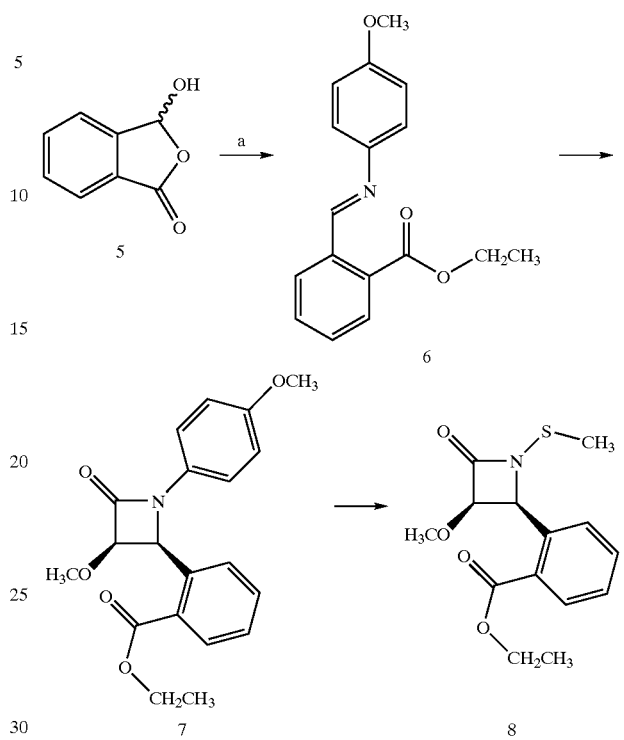

$^a$Conditions: (a) (i) CH$_3$CH$_2$I, K$_2$CO$_3$, acetone (ii) p-anisidine, Et$_3$N, CH$_2$Cl$_2$. (b) CH$_3$OCH$_2$COCl, Et$_3$N, CH$_2$Cl$_2$. (c) (i) (NH$_4$)$_2$Ce(NO$_3$)$_6$, CH$_3$CN—H$_2$O; (ii) N-methylthio phthalimide, Et$_3$N, CH$_2$Cl$_2$ In addition to these C-3 methoxy-substituted lactams, the corresponding C-3 acetoxy analogues are also studied. Scheme III summarizes the synthesis of these β-lactams. In same cases, both cis-10 and trans-10' adducts can be obtained and separated for biological studies.

Scheme III

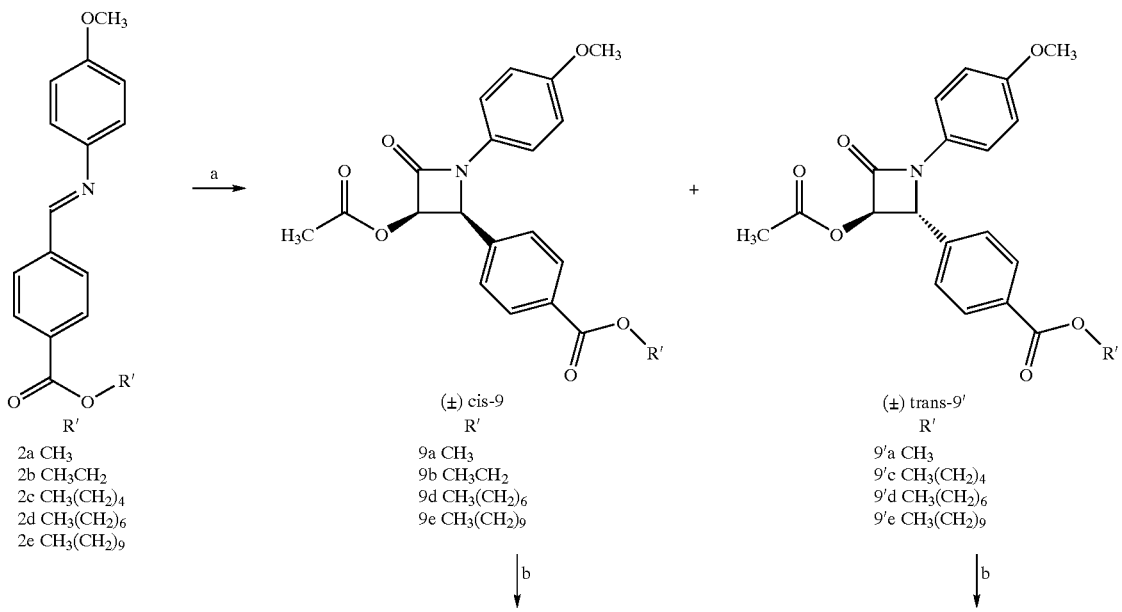

-continued

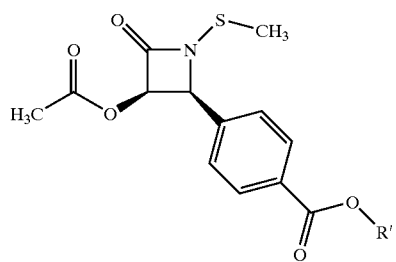

(±) cis-10

| R' | |
|---|---|
| 10a | CH₃ |
| 10b | CH₃CH₂ |
| 10d | CH₃(CH₂)₆ |
| 10e | CH₃(CH₂)₉ |

+

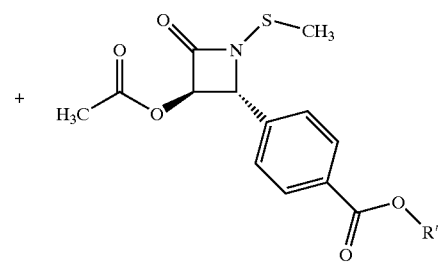

(±) trans-10'

| R' | |
|---|---|
| 10'a | CH₃ |
| 10'b | CH₃CH₂ |
| 10'd | CH₃(CH₂)₆ |
| 10'e | CH₃(CH₂)₉ |

<sup>a</sup>Conditions: (a) CH₃C(O)OCH₂COCl, Et₃N, CH₂Cl₂. (b) (i) (NH₄)₂Ce(NO₃)₆, CH₃CN—H₂O; (ii) N-methylthio phthalimide, Et₃N, CH₂Cl₂.

While the invention has been described in terms of various preferred embodiments, those skilled in the art will recognize that various modifications, substitutions, omissions, and changes may be made without departing from the spirit of the present invention. Accordingly, it is intended that the scope of the present invention be limited solely by the scope of the following claims.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

What is claimed is:

1. A N-1 thiolated monobactam compound of the formula:

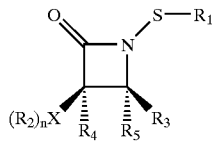

or a salt or hydrate thereof, wherein:
$R_1$ is alkyl, cycloalkyl, heteroalkyl, aryl, or heteroaryl;
$X(R_2)_n$ is hydrogen, methoxy, acetoxy, or phenoxy;
$R_3$ is aryl($C_1$–$C_6$)alkyl, aryl($C_2$–$C_6$)alkenyl, aryl, heteroalkyl, heteroaryl; wherein any aryl or heteroaryl is optionally substituted with halo, nitro, cyano, hydroxyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_1$–$C_{15}$)alkoxy, ($C_3$–$C_8$)cycloalkyl-($C_2$–$C_{15}$)alkenyl, ($C_3$–$C_8$)cycloalkyl($C_2$–$C_{15}$)alkynyl, ($C_1$–$C_{15}$)alkoxy, ($C_1$–$C_{15}$)alkanoyl, ($C_1$–$C_{15}$) alkanoyloxy, C(O)O($C_1$–$C_6$)alkyl, C(=O)N(($C_1$–$C_6$) alkyl)₂, or N(($C_1$–$C_6$)alkyl)₂;
$R_4$ is hydrogen;
$R_5$ is hydrogen; and
excluding the compounds 3-methoxy-1-methylthio-4-phenylethynyl-2-oxoazetidine, and 1-thiomethyl-3-methoxy-4-(O-acctyl)phenylethynyl-2-oxoazetidine.

2. The compound of claim 1, wherein the N-1 thiolated monobactam compound is selected from the group consisting of:

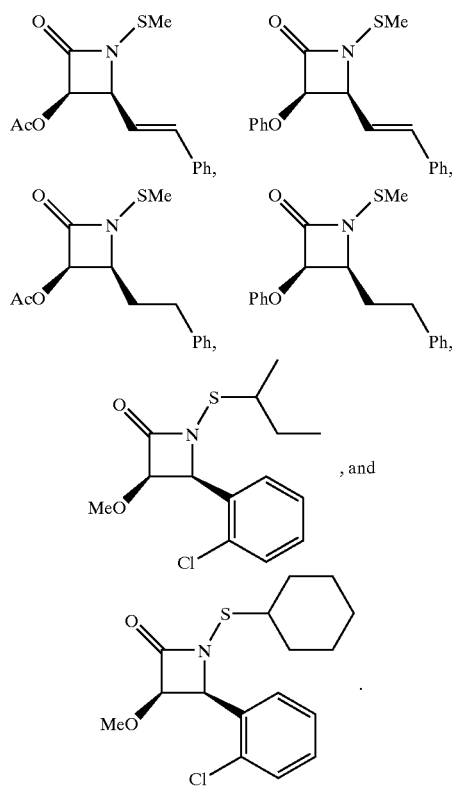

3. A method for inhibiting bacterial infection comprising administering the N-1 thiolated monobactam compound of claim 1, or a salt or a hydrate thereof, to a patient in an effective amount to inhibit the infection, wherein the infection is caused by a bacterium selected from the group consisting of *Staphylococcus* spp., *M. luteus, N. gonorrhoeae, Bacteroides fragelis,* and *Haemophilus influenzae* 561.

4. The method of claim 3, wherein the bacterium is selected from the group consisting of *Staphylococcus aureus, Staphylococcus epidermis,* and *Staphylococcus simulans.*

5. The method of claim 3, wherein the bacterium is a methicillin-resistant *Staphylococcus*.

6. The method of claim 3, wherein the bacterium is selected from the group consisting of MRSA USF652, MRSA USF653, MRSA USF654, MRSA US655, MRSA USF656, MRSA USF657, MRSA USF658, and MRSA USF659.

7. The method of claim 3, wherein the N-1 thiolated monobactam compound is selected from the group consisting of

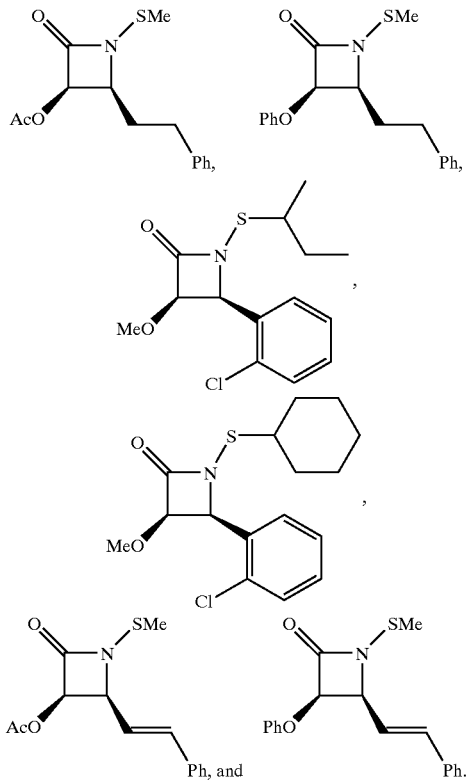

8. The method of claim 3, wherein the N-1 thiolated monobactam compound of claim 1, or a salt or a hydrate thereof, is administered in a pharmaceutically acceptable carrier.

9. A method of inhibiting growth of a bacterium comprising administering an effective amount of a N-1 thiolated monobactam, or a salt or a hydrate thereof, to the bacterium, wherein the bacterium is selected from the group consisting of *Staphylococcus* spp., *M. luteus, N. gonorrhoeae, Bacteroides fragelis*, and *Haemophilus influenzae* 561.

10. The method of claim 9, wherein the bacterium is selected from the group consisting of *Staphylococcus aureus, Staphylococcus epidermis*, and *Staphylococcus simulans*.

11. The method of claim 5, wherein the bacterium is a methicillin-resistant *Staphylococcus*.

12. The method of claim 9, wherein the bacterium is selected from the group consisting of MRSA USF652, MRSA USF653, MRSA USF654, MRSA USF655, MRSA USP656, MRSA USF657, MRSA USF658, and MRSA USF659.

13. A N-1 thiolated monobactam compound of the formula:

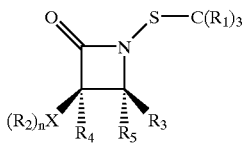

or a salt or hydrate thereof, wherein:

—$C(R_1)_3$ is alkyl or heteroalkyl;

—$X(R_2)_n$ is $OSO_2R_6$;

$R_3$ is alkynyl, alkenyl, acetyl, aryl, heteroaryl, aryl($C_1$–$C_6$)alkyl, heteroaryl($C_1$–$C_6$)alkyl, aryl($C_2$–$C_6$)alkenyl, heteroaryl($C_2$–$C_6$)alkenyl, aryl($C_2$–$C_6$)alkynyl or heteroaryl($C_2$–$C_6$)alkynyl; wherein any aryl or heteroaryl is optionally substituted with halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_1$–$C_{15}$)alkoxy, ($C_3$–$C_8$)cycloalkyl-($C_2$–$C_{15}$)alkenyl, ($C_3$–$C_8$)cycloalkyl($C_{21}$–$C_{15}$)alkynyl, ($C_1$–$C_{15}$)alkoxy, ($C_1$–$C_{15}$)alkanoyl, ($C_1$–$C_{15}$)alkanoyloxy, C(O)O($C_1$–$C_6$)alkyl, C(=O)N(($C_1$–$C_6$)alkyl)$_2$, or N(($C_1$–$C_6$)alkyl)$_2$;

$R_4$ is hydrogen;

$R_5$ is hydrogen; and $R_6$ is alkyl, aryl, or heteroaryl, wherein any aryl or heteroaryl is optionally substituted with halo, nitro, cyano, hydroxy, trifluoromethyl, trifluoromethoxy, ($C_1$–$C_{15}$)alkyl, ($C_2$–$C_{15}$)alkenyl, ($C_2$–$C_{15}$)alkynyl, ($C_3$–$C_8$)cycloalkyl, ($C_3$–$C_8$)cycloalkyl($C_2$–$C_{15}$)alkoxy, ($C_3$–$C_8$)cycloalkyl-($C_2$–$C_{15}$)alkenyl, ($C_3$–$C_8$)cycloalkyl($C_{21}$–$C_{15}$)alkynyl, ($C_1$–$C_{15}$)alkoxy, ($C_1$–$C_{15}$)alkanoyl, ($C_1$–$C_{15}$)alkanoyloxy, C(O)O($C_1$–$C_6$)alkyl, C(=O)N(($C_1$–$C_6$)alkyl)$_2$, or N(($C_1$–$C_6$)alkyl)$_2$.

14. The compound of claim 13, wherein said compound is selected from the group consisting of:

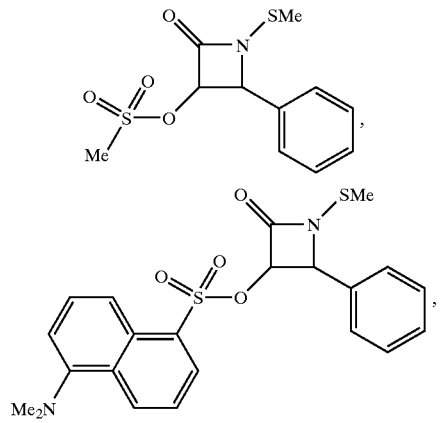

27
-continued
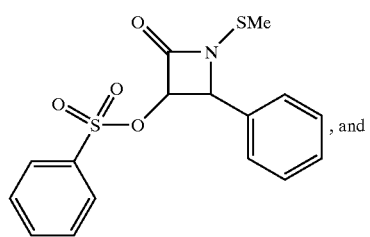
, and
28
-continued
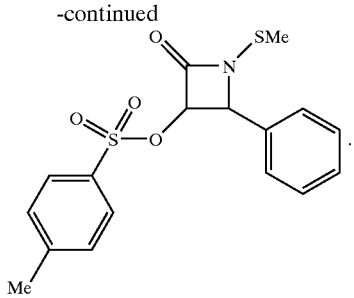
.
\* \* \* \* \*

UNITED STATES PATENT AND TRADEMARK OFFICE
CERTIFICATE OF CORRECTION

PATENT NO. : 6,946,458 B2
APPLICATION NO. : 10/288897
DATED : September 20, 2005
INVENTOR(S) : Edward Turos It is certified that error appears in the above-identified patent and that said Letters Patent is hereby corrected as shown below:

(57) Abstract,
"specially" should read -- specifically --.
"aureaus" should read -- aureus --.

Column 2,
Line 39, "β-lactamases; enzymes" should read -- β-lactamases: enzymes --.

Column 17,
Table 5, "S.aureus 525" should read -- S. aureus 525 --.

Column 20,
Line 65, "(c) $(NH_4)_2Ce(NO_3)_6$," should read -- (c) (i) $(NH_4)_2Ce(NO_3)_6$, --.

Columns 21 and 22,
Scheme III:
"  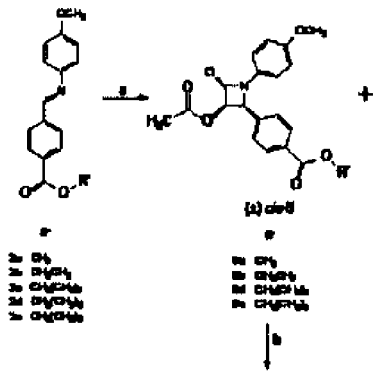  "  should read  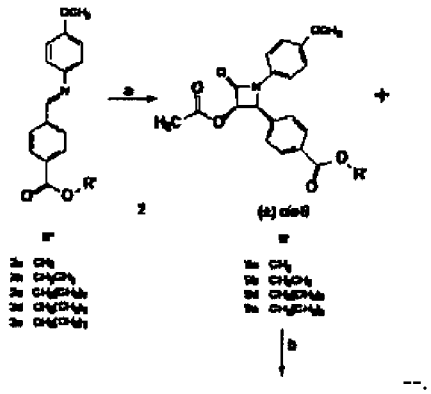  --.

Column 23,
Line 67, "(O-acctyl)" should read -- (O-acetyl) --.

Column 25,
Line 5, "US655" should read -- USF655 --.
Line 66, "USP656" should read -- USF656 --.

UNITED STATES PATENT AND TRADEMARK OFFICE
CERTIFICATE OF CORRECTION

PATENT NO.         : 6,946,458 B2
APPLICATION NO. : 10/288897
DATED                  : September 20, 2005
INVENTOR(S)       : Edward Turos It is certified that error appears in the above-identified patent and that said Letters Patent is hereby corrected as shown below:

Column 26,
Line 29, "cycloalkyl($C_{21}$-$C_{15}$)" should read -- cycloalkyl($C_2$-$C_{15}$) --.
Line 41, "($C_3$-$C_8$)cycloalkyl($C_2$-$C_{15}$)alkoxy" should read
-- ($C_3$-$C_8$)cycloalkyl($C_1$-$C_{15}$)alkoxy --.
Line 43, "cycloalkyl($C_{21}$-$C_{15}$)" should read -- cycloalkyl($C_2$-$C_{15}$) --.

Signed and Sealed this

Sixteenth Day of June, 2009

JOHN DOLL
*Acting Director of the United States Patent and Trademark Office*

UNITED STATES PATENT AND TRADEMARK OFFICE
Certificate

Patent No. 6,946,458 B2                            Patented: September 20, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Edward Turos, Temple Terrace, FL (US); Sonja S. Dickey, Tampa, FL (US); Daniel V. Lim, Tampa, FL (US); and Timothy Long, Tampa, FL (US).

Signed and Sealed this Twenty-first Day of February 2012.

JAMES O. WILSON
*Supervisory Patent Examiner*
Art Unit 1624
Technology Center 1600